(12) United States Patent
Ständker et al.

(10) Patent No.: US 8,299,031 B2
(45) Date of Patent: Oct. 30, 2012

(54) HUMAN SEMEN ENHANCER OF VIRAL INFECTION PEPTIDES (SEVI) AND THEIR USE

(75) Inventors: Ludger Ständker, Hannover (DE); Wolf-Georg Forssmann, Wies-Wambach (DE); Knut Adermann, Hannover (DE); Jan Münch, Ulm (DE); Frank Kirchhoff, Ulm (DE); Elke Rücker, Dresden (DE)

(73) Assignee: Viro Pharmaceuticals GmbH & Co. KG, Hannover (DE)

( * ) Notice: Subject to any disclaimer, the term of this patent is extended or adjusted under 35 U.S.C. 154(b) by 186 days.

(21) Appl. No.: 12/162,093

(22) PCT Filed: Jan. 25, 2007

(86) PCT No.: PCT/EP2007/050727
§ 371 (c)(1), (2), (4) Date: Dec. 29, 2008

(87) PCT Pub. No.: WO2007/085630
PCT Pub. Date: Aug. 2, 2007

(65) Prior Publication Data
US 2009/0191206 A1 Jul. 30, 2009

(30) Foreign Application Priority Data
Jan. 25, 2006 (EP) .................. 06100818

(51) Int. Cl.
*A61K 38/16* (2006.01)
*A61K 39/00* (2006.01)
*C12N 7/01* (2006.01)
*C12N 15/867* (2006.01)

(52) U.S. Cl. ............... 514/21.3; 424/184.1; 435/235.1; 435/456

(58) Field of Classification Search .............. None
See application file for complete search history.

(56) References Cited

U.S. PATENT DOCUMENTS
5,976,546 A 11/1999 Laus et al.

FOREIGN PATENT DOCUMENTS
WO WO 03/040165 * 5/2003
WO WO 2005/090560 A1 9/2005

OTHER PUBLICATIONS

GenBank X53605, "Human mRNA for prostatic acid phosphatase,",Sep. 1993.*
Munch, J. et al., "Semen-Derived Amyloid Fibrils Drastically Enhance HIV Infection", Dec. 2007, Cell, vol. 131: pp. 1059-1071.*
Chakraborty et al., "Viral buden in genital secretions determines male-to-female sexual transmission of HIV-1: a probabilistic empiric model", 2001, AIDS, vol. 15: pp. 621-627.*
Hemminga, M. et al., "Virusees: incredible nanomachines. New advances with filamentous phages", 2010, Eur. Biophys. J., vol. 39: pp. 541-550.*
Sharma, A. et al., "Adenovirus receptors and their implications in gene delivery", 2009, Vir. Res., vol. 143: pp. 184-194.*
Adachi, A., et al., "Production of Acquired Immunodeficiency Syndrome-Associated Retrovirus in Human and Nonhuman Cells Transfected with an Infectious Molecular Clone," *J. Virol.* 59:284-291, American Society for Microbiology (1986).
Apostol, I., et al., "Phosphotyrosine as a substrate of acid and alkaline phosphatases," *Acta Biochim. Pol.* 32:187-197, Polish Biochemical Society (1985).
Aumüller, G. And Seitz, J. "Cytochemistry and Biochemistry of Acid Phosphatases. VI: Immunoelectron Microscopic Studies on Human Prostatic and Leukocytic Acid Phosphatases," *Prostate* 7:161-169, Alan R. Liss, Inc. (1985).
Baribaud, F., et al., "Quantitative Expression and Virus Transmission Analysis of DC-Sign on Monocyte-Derived Dendritic Cells," *J. Virol.* 76:9135-9142, American Society for Microbiology (2002).
Briggs, J.A.G., et al., "The stoichiometry of Gag protein in HIV-1," *Nat. Struct. Mol. Biol.* 11:672-675, Nature Publishing Group (2004).
Chantry, D. "HIV entry and fusion inhibitors," *Expert Opin. Emerg. Drugs* 9:1-7, Ashley Publications Ltd. (2004).
Charneau, P., et al., "Isolation and Envelope Sequence of a Highly Divergent HIV-1 Isolate: Definition of a New HIV-1 Group," *Virol.* 205:247-253, Academic Press (1994).
Choe, B.K., et al., "Expression of human prostatic acid phosphatase in a pancreatic islet cell carcinoma," *Invest. Urol.* 15:312-318, The Williams and Wilkins Co. (1978).
Choe, B.K., et al., "Double-Antibody Immunoenzyme Assay for Human Prostatic Acid Phosphatase," *Clin. Chem.* 26:1854-1859, American Association for Clinical Chemistry (1980).
Clavel, F., et al., "Molecular cloning and polymorphism of the human immune deficiency virus type 2," *Nature* 324:691-695, Nature Publishing Group (1986).
Coffey, D.S. and Pienta, K.J. "New concepts in studying the control of normal and cancer growth of the prostate," *Prog. Clin. Biol. Res.* 239:1-73, Alan R. Liss, Inc. (1987).
Cronin, J., et al., "Altering the Tropism of Lentiviral Vectors through Pseudotyping," *Curr. Gene Ther.* 5:387-398, Bentham Science Publishers Ltd. (Aug. 2005).
Cusan, L., et al., "Metastatic Prostate Cancer Pulmonary Nodules: Beneficial Effects of Combination Therapy and Subsequent Withdrawal of Flutamide," *Prostate* 24:257-261, Wiley-Liss, Inc. (1994).
Derechin, M., et al., "Acid phosphomonoesterase of human prostate. Molecular weight, dissociation and chemical composition," *Biochim. Biophys. Acta* 250:143-154, Elsevier Publishing Co. (1971).

(Continued)

Primary Examiner — Michael Burkhart
(74) Attorney, Agent, or Firm — Sterne, Kessler, Goldstein & Fox P.L.L.C.

(57) ABSTRACT

Subject of the invention are peptides corresponding to a fragment of amino acids 240-290 of human prostatic acid phosphatase. The invention also relates to nucleic acids, antibodies, medicaments and diagnostics and their use and use of the peptides for the treatment and diagnosis of viral diseases, especially HIV disease.

15 Claims, 21 Drawing Sheets

OTHER PUBLICATIONS

Figure 1:
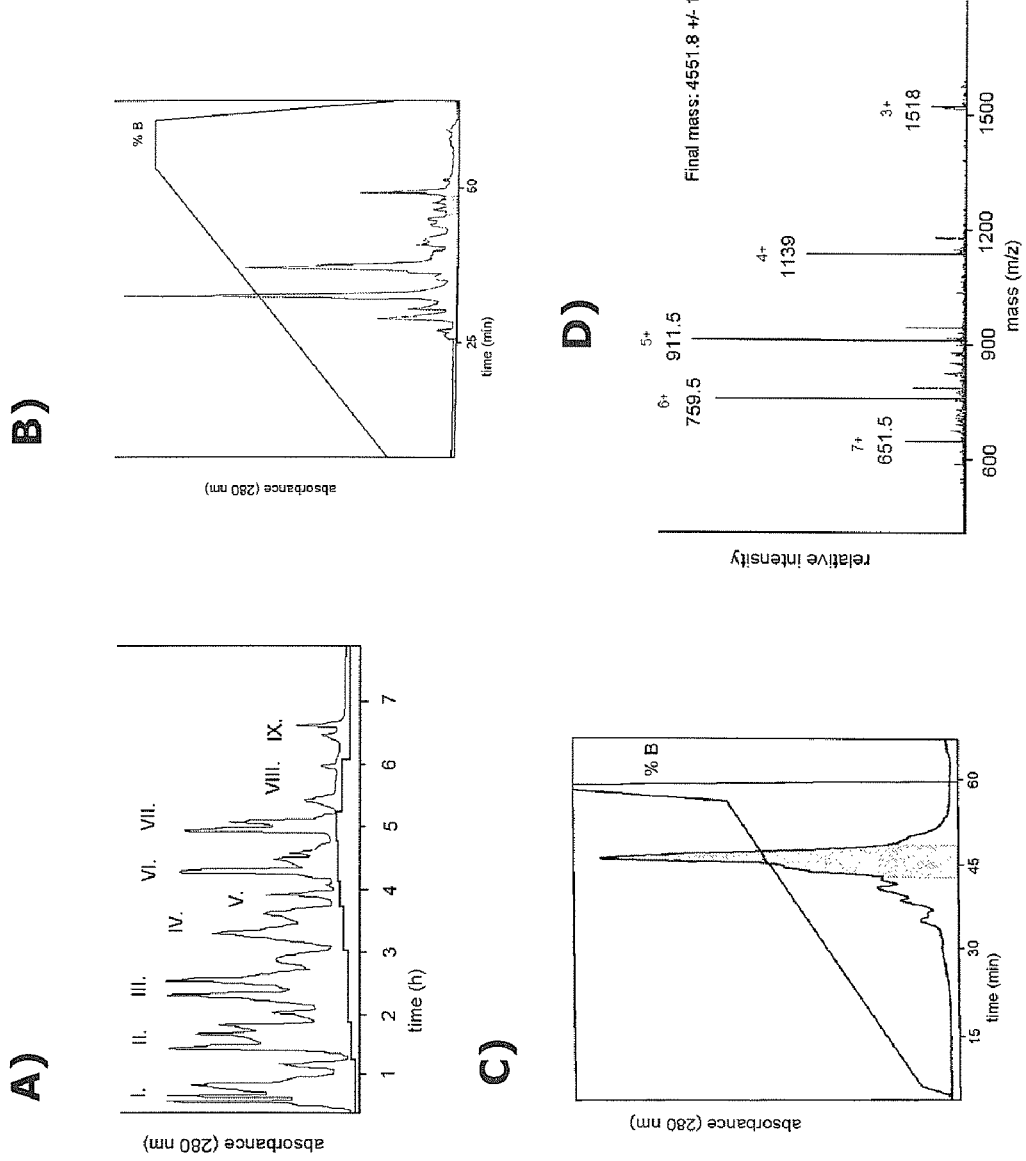

Dittmar, M.T., et al., "Coreceptor Requirements of Primary HIV Type 1 Group O Isolates from Cameroon," *AIDS Res. Hum. Retroviruses* 15:707-712, Mary Ann Liebert, Inc. (1999).

Drenckhahn, D., et al., "Demonstration of prostatic-type acid phosphatase in non-lysosomal granules in the crypt epithelium of the human duodenum," *Histochemistry* 88:47-52, Springer-Verlag (1987).

Dziembor-Gryszkiewicz, E., et al., "Activity of Human Prostatic Acid Phosphatase Toward Purine 5'-Phosphonucleosides," *Bull. Acad. Pol. Sci. Biol.* 26:815-821, Polska Akademia Nauk (1978).

Griffiths, J.C. "Prostate-Specific Acid Phosphatase: Re-Evaluation of Radioimmunoassay in Diagnosing Prostatic Disease," *Clin. Chem.* 26:433-436, American Association for Clinical Chemistry (1980).

Gundlach, B.R., et al., "Env-Independent Protection Induced by Live, Attenuated Simian Immunodeficiency Virus Vaccines," *J. Virol.* 72:7846-7851, American Society for Microbiology (1998).

Hakalahti, L., et al., "Evaluation of PAP and PSA gene expression in prostatic hyperplasia and prostatic carcinoma using northern-blot analyses, in situ hybridization and immunohistochemical stainings with monoclonal and bispecific antibodies," *Int. J. Cancer* 55:590-597, Wiley-Liss, Inc. (1993).

He, J. and Landau, N.R. "Use of a Novel Human Immunodeficiency Virus Type 1 Reporter Virus Expressing Human Placental Alkaline Phosphatase to Detect an Alternative Viral Receptor," *J. Virol.* 69:4587-4592, American Society for Microbiology (1995).

Kamoshida, S. and Tsutsumi, Y. "Extraprostatic Localization of Prostatic Acid Phosphatase and Prostate-Specific Antigen: Distribution in Cloacogenic Glandular Epithelium and Sex-Dependent Expression in Human Anal Gland," *Hum. Pathol.* 21:1108-1111, W.B. Saunders Company (1990).

Kuciel, R., et al., "Is the subunit of prostatic phosphatase active? Reversible denaturation of prostatic acid phosphatase," *Biochem. Int.* 22:329-334, Academic Press Australia (1990).

Lee, C.L, et al., "Immunologically reactive tryptic fragments of human prostatic acid phosphate," *Biochem. J.* 223:871-877, Portland Press on behalf of the Biochemical Society (1984).

Luchter-Wasyl, E. and Ostrowski, W. "Subunit structure of human prostatic acid phosphatase," *Biochim. Biophys. Acta* 365:349-359, Elsevier Scientific Publishing Company (1974).

McNeel, D.G., et al., "Identification of T Helper Epitopes from Prostatic Acid Phosphatase," *Cancer Res.* 61:5161-5167, American Association for Cancer Research (2001).

Münch, J., et al., "Hemofiltrate CC Chemokine 1[9-74] Causes Effective Internalization of CCR5 and Is a Potent Inhibitor of R5-Tropic Human Immunodeficiency Virus Type 1 Strains in Primary T Cells and Macrophages," *Antimicrob. Agents Chemother.* 46:982-990, American Society for Microbiology (2002).

Nilsson, M.R. "Techniques to study amyloid fibril formation in vitro," *Methods* 34:151-160, Elsevier Inc. (2004).

Papkalla, A., et al., "Nef Enhances Human Immunodeficiency Virus Type 1 Infectivity and Replication Independently of Viral Coreceptor Tropism," *J. Virol.* 76:8455-8459, American Society for Microbiology (2002).

Peshwa, M.V., et al., "Induction of Prostate Tumor-Specific CD8+ Cytotoxic T-Lymphocytes in Vitro Using Antigen-Presenting Cells Pulsed With Prostatic Acid Phosphatase Peptide," *Prostate* 36:129-138, Wiley-Liss, Inc. (1998).

Pöhlmann, S., et al., "Coreceptor usage of BOB/GPR15 and Bonzo/STRL33 by primary isolates of human immunodeficiency virus type 1," *J. Gen. Virol.* 80:1241-1251, Society for General Microbiology (1999).

Risley, J.M. and Van Etten, R.L. "Structures of the Carbohydrate Moieties of Human Prostatic Acid Phosphatase Elucidated by $^1$H Nuclear Magnetic Resonance Spectroscopy," *Arch. Biochem. Biophys.* 258:404-412, Academic Press, Inc. (1987).

Rönnberg, L., et al., "Clomiphene citrate administration to normogonadotropic subfertile men: Blood hormone changes and activation of acid phosphatase in seminal fluid," *Int. J. Androl.* 4:372-378, Blackwell Publishers (1981).

Schiff, D., et al., "Bilirubin Toxicity in Neural Cell Lines N115 and NBR10A," *Pediatr. Res.* 19:908-911, International Pediatric Research Foundation, Inc. (1985).

Sharief, F.S. and LI, S.S.-L., "Structure of human prostatic acid phosphatase gene," *Biochem. Biophys. Res. Commun.* 184:1468-1476, Academic Press, Inc. (1992).

Shaw, L.M., et al., "Immunochemical Evaluation of the Organ Specificity of Prostatic Acid Phosphatase," *Clin. Chem.* 27:1505-1512, American Association for Clinical Chemistry (1981).

Vihko, P., et al., "Purification of Human Prostatic Acid Phosphatase by Affinity Chromatography and Isoelectric Focusing. Part I," *Clin. Chem.* 24:466-470, American Association for Clinical Chemistry (1978).

Vihko, P. "Characterization of the Principal Human Prostatic Acid Phosphatase Isoenzyme, Purified by Affinity Chromatography and Isoelectric Focusing. Part II," *Clin. Chem.* 24:1783-1787, American Association for Clinical Chemistry (1978).

Vihko, P., et al., "Rapid radioimmunoassay for prostate-specific acid phosphatase in human serum," *Clin. Chem.* 26:1544-1547, American Association for Clinical Chemistry (1980).

Vihko, P., et al., "Effectiveness of Radioimmunoassay of Human Prostate-specific Acid Phosphatase in the Diagnosis and Follow-up of Therapy in Prostatic Carcinoma," *Cancer Res.* 41:1180-1183, American Association for Cancer Research (1981).

Vihko, P., et al., "Molecular cloning and sequence analysis of cDNA encoding human prostatic acid phosphatase," *FEBS Lett.* 236:275-281, Elsevier Science Publishers B.V. (1988).

Vihko, P., et al., "Rat acid phosphatase: Overexpression of active, secreted enzyme by recombinant baculovirus-infected insect cells, molecular properties, and crystallization," *Proc. Natl. Acad. Sci. USA* 90:799-803, National Academy of Sciences (1993).

Waheed, A. and Van Etten, R.L. "Biosynthesis and Processing of Lysosomal Acid Phosphatase in Cultured Human Cells," *Arch. Biochem. Biophys.* 243:274-283, Academic Press, Inc. (1985).

Wasylewska, E., et al., "Phosphoprotein phosphatase activity of human prostate acid phosphatase," *Acta Biochim. Pol.* 30:175-184, Panstwowe Wydawnictwo Naukowe (1983).

Wei, X., et al., "Emergence of Resistant Human Immunodeficiency Virus Type 1 in Patients Receiving Fusion Inhibitor (T-20) Monotherapy," *Antimicrob. Agents Chemother.* 46:1896-1905, American Society for Microbiology (2002).

Westermark, P. "Aspects on human amyloid forms and their fibril polypeptides," *FEBS J.* 272:5942-5949, The Authors Journal compilation and FEBS (Dec. 2005).

Wojtowicz, W.M., et al., "Stimulation of Enveloped Virus Infection by β-Amyloid Fibrils," *J. Biol. Chem.* 277:35019-35024, The American Society for Biochemistry and Molecular Biology, Inc. (2002).

Yam, L.T., et al., "Presence of 'prostatic' acid phosphatase in human neutrophils," *Invest. Urol.* 19:34-38, The Williams & Wilkins Co. (1981).

International Search Report and Written Opinion for International Application No. PCT/EP2007/050727, mailed on Jun. 8, 2007, European Patent Office, Rijswijk, Netherlands.

\* cited by examiner

C

B

A

C

B

A

HUMAN SEMEN ENHANCER OF VIRAL INFECTION PEPTIDES (SEVI) AND THEIR USE

This application is a U.S. National Stage of International Application No. PCT/EP2007/050727, filed Jan. 25, 2007, which claims the benefit of European Patent Application No. 06100818.1, filed Jan. 25, 2006.

Subject of the invention are peptides, nucleic acids, antibodies, medicaments and diagnostics and their use for the treatment and diagnosis of viral diseases, and the improvement of diagnostic methods, of virus isolation techniques and of transduction efficiencies with retroviral vectors in ex vivo and in vivo gene therapy.

There is a continuing need for alternative and improved medicaments against viral infections such as HIV infection, especially HIV-1 transmission. Even though various medications against HIV were developed in the past years, infections with HIV are still a world wide problem. For many viral diseases like AIDS, caused by HIV, a cure is still not available. There is also a need for easy and efficient methods of diagnosis and for laboratory tools to study and understand the viruses.

Gene therapy approaches are often hampered by low transduction efficiencies of target cells, especially stem cells, by retroviral vectors. The transduction efficiency is crucial for efficient gene transfer into the target cell and is usually low when retroviral vectors are used for gene transfer in stem cells. Thus, there is also a need for an improved retroviral transduction system for successful delivery of the gene in appropriate cells.

The problem underlying the present invention is to provide improved or alternative medication, diagnostic tools and laboratory tools which overcome the above mentioned problems associated with viral diseases and gene therapy.

Surprisingly, the problem underlying the present invention is solved by peptides, nucleic acids, antibodies, medicaments, diagnostics and uses of any of claims 1-15.

The amino acid sequence of the peptides of the invention is represented by the formula $$R^1\text{-KEKSRLQGGVLVNEILNHMKRATQIPSYKK-}R^2$$

wherein
$R^1$ is H, YGIHKQ, GIHKQ, IHKQ, HKQ, KQ or Q
and $R^2$ is independently —COOH, LIMY, LIM, LI, L,
except a peptide of Seq. ID No. 18.

In particular, peptides of the invention are those of Seq. ID No. 1 to Seq. ID No. 12.

The peptides of the invention are fragments of the amino acid residues 240-290 of human prostatic acid phosphatase (hPAP) except a peptide of Seq. ID No. 18, more preferably of residues 247-286, which promote viral infection of a cell. The numbering refers to the protein sequence in its unprocessed form, including the pro-sequence. The human prostatic acid phosphatase (hPAP; Swissprot: locus PPAP_HUMAN, accession P15309) in its processed form consists of 354 amino acids with a calculated molecular mass of 41126 Da (Vihko et al.; 1988, Sharief & Li; 1992). The protein hPAP itself and the nucleic acid encoding it are not subject of the invention. D. G. Mc Neel et al. report in Cancer Research 61, 5161-5167 (2001) about the identification of T helper epitopes from prostatic acid phosphatase. The present invention is based on the discovery that hPAP fragments can form amyloid like fibrilar structures that enhance the infectivity of cells by the human immunodeficiency virus (HIV) and other enveloped viruses.

In the following, the inventive peptides in their fibrilar, amyloid-like form are referred to as "SEVI" peptides or simply "SEVI" for "Semen Enhancer of Viral Infections". PAP fragments form amyloid-like fibrilar structures when dissolved in $H_2O$, cell culture medium or conventional buffers such as PBS, either spontaneously or after agitation. In general, peptides with partial sequences of the 51 residue section of amino acids 240-290 of the hPAP amino acid sequence are subject of the invention. Preferably, the peptides comprise at least 12, in other embodiments at least 20, 25, 30 or 38 amino acids. The peptides comprise no more than 50, preferably no more than 47 or 45 amino acids. Especially preferred are the peptides SEVI 1-12 of amino acid sequences SEQ ID No. 1 to 12.

Further embodiments of the invention are peptides derived from SEVI peptides with at least one of the following sequence variations:
- a deletion of amino acids at the N- and/or C-terminus, wherein the peptide consists of at least 30, preferably 35 to 38 amino acids.
- an addition of up to 10 amino acids, preferably 1, 2, 3 or 5 amino acids at the N- and/or C-terminus.
- an amino acid exchange of up to 5, preferably of 1, 2 or 3 amino acids; the amino acid exchange being preferably a conservative exchange.
- an amino acid insertion or deletion within the sequence of up to 3, preferably 2 or 1 amino acids.

In a conservative amino acid exchange, an amino acid is replaced by another amino acid with similar properties. Conservative amino acid exchanges are preferably within any one of the groups of
Amino acids with unpolar side chains: A, G, V, L, I, P, F, W, M
Uncharged amino acids with polar side chains: S, T, G, C, Y, N, Q
Amino acids with aromatic side chains: F, Y, W
Positively charged amino acids: K, R, H
Negatively charged amino acids: D, E.

Further embodiments of the invention are peptides derived from SEVI peptides or their derivatives as outlined above with at least one of the following covalent modifications:
- acylation, acetylation, linkage to a non-peptidic macromolecular carrier group; preferably at the N-terminus.
- amidation, linkage to a non-peptidic macromolecular carrier group; preferably at the C-terminus
- glycosylation; preferably at amino acid side chains.
- linkage to an adaptor protein, which promotes uptake of the peptide into cells or linkage to a hydrophobic group, preferably a lipid, a fatty acid, a dansyl, a carbobenzoxyl or a t-butyloxycarbonyl group.
- oxidation, sulphatization, esterification, lactone formation and/or phosphorylation.

Preferred macromolecular carrier groups are polyethylene glycol (PEG), polyoxyalkylene glycol, polysorbate esters, mannan, amylopectin, pullulan, hydrogelnanoparticles of self aggregated hydrophobized polysaccharides, polylysine or albumine.

Subject of the invention are also retro, inverso or retro-inverso peptides of SEVI peptides and peptides obtainable by multiple synthesis which have the biological activity of SEVI peptides. The peptides may comprise at least on D-amino acid as well as iminoamino acids and rare amino acids, such as hydroxylysine, homoserine and ornithine. The invention also relates to peptide mimetics of the peptides according to the invention. These are characterized by a modification of one or more peptide bonds, for example, by a reverse peptide bond or by an ester bond.

The peptides of the invention promote viral infection of a cell. As used herein, "viruses" relates to natural occurring viruses and virus particles as well as artificial viruses and virus particles, which may for instance comprise a nucleic acid designed for gene therapy. In preferred embodiments, the viruses are retroviruses and retroviral particles such as oncoviruses, lentiviruses and foamy viruses. Generally, the peptides of the invention are especially useful to enhance infection of target cells with replication competent viruses. Specific viruses are HIV-1 (Human Immunodeficiency Virus Typ 1), HIV-2, Simian Immunodeficiency Viruses (SIV) as well as the oncovirus Murine Leukemia Virus (MuLV) and Foamy Virus. The peptides also promote the infection of HIV-variants, such as X4, R5 and dual-tropic variants, molecular HIV clones and HIV-1 subtypes. The peptides also favour infection with Hepatitis B Virus (HBV) or retroviral particles that were pseudotyped with heterologous envelope proteins derived from Vesicular Stomatitis Virus (VSV), MuLV, Ebola, HIV-1 and MuLV. Therefore the peptides of the invention increase transduction efficiencies of retrovirus based gene therapy systems.

In other preferred embodiments of the invention, the peptides favour infections with flaviviruses such as yellow fever virus, Dengue virus, West-Nile virus, tick-borne encephalitis virus, hepatitis C and G virus, swine fever virus, with toga viruses such as rubella virus, with corona viruses such as SARS virus, with caliciviruses such as Norwalk virus and hepatitis E virus, with rhabdoviruses such as vesicular stomatitis Indiana virus and rabies virus, with paramyxoviruses such as human parainfluenza virus I, mumps virus, measles virus and human respiratory syncytial virus, with filoviruses such as Marburg virus and Ebola virus, with orthomyxoviruses such as influenza A/B/C viruses, with arenaviruses such as Lassa virus, with herpesviruses such as herpes simplex viruses 1 and 2, varizella zoster virus, cytomegalovirus, Epstein-Barr virus, human herpesviruses 6, 7 and 8, with poxviruses such as vaccinia virus, with reoviruses such as rotaviruses, with picornaviruses such as poliovirus, rhinovirus, hepatitis A virus, encephalomyocarditis virus and foot-and-mouth disease virus, with papovaviruses such as polyomaviruses and pappilom virus, and with adenoviruses.

The activity of the peptides can be measured for instance in a luciferase assay or in a GFP expression assay. Preferably, the peptides, for instance at a concentration of 1 or 5 μg/ml, enhance viral infection into cells at least by a factor of 2, more preferred by a factor of 3, 5 or 10 when compared to viral infection into the cells in the absence of the peptide. When target cells are infected with a low multiplicity of infection, usually SEVI enhances viral infection rates by several orders of magnitude.

Subject of the invention are also nucleic acids coding for the peptides of the invention and expression vectors for the inventive peptides, such as plasmids, cosmids and viral vectors.

Another subject of the invention is the generation and use of specific antibodies against the inventive peptide. Preferably, they are used as therapeutics. They block the activity of SEVI peptides, and for instance hamper the transmission of viral particles in vivo, like sexual transmitted viral diseases, especially diseases transmitted by HIV-1 or HIV-2 or HBV. The inventive antibodies are obtainable by known methods such as isolation from a serum or monoclonal antibody technology. The conventional method is to inject a laboratory animal with an antigen and then, after antibodies had been formed, collect those polyclonal antibodies from the blood serum. In monoclonal antibody technology, tumor cells like myeloma cells that can replicate endlessly are fused with mammalian cells to a hybridoma that continually produces the antibodies.

hPAP is synthesized in epithelial cells of the prostate gland (Ostrowski et al.; 1976, Risley & van Etten; 1987, Hakalahti et al.; 1993), and is secreted into the prostatic fluid (Vihko; 1978, Vihko et al.; 1978a, 1978b). hPAP hydrolyzes alkyl and aryl orthophosphate monoesters, including phosphotyrosine (Apostol et al.; 1985; Vihko et al.; 1993) and nucleotides (Dziembor-Gryszkiewicz et al.; 1978), and has also been found to dephosphorylate macromolecules, such as phosphopeptides and phosphoproteins (Wasylewska et al.; 1983, Li et al.; 1984). Due to its pH optimum of 4-6, hPAP is categorized as an acid phosphatase.

In the 5'-end, the cDNA codes for a signal peptide of 32 amino acids. Native hPAP exists as a dimer (Derechin et al.; 1971, Luchter-Wasyl & Ostrowski 1974, Vihko et al.; 1978) of two catalytically inactive subunits non-covalently bound together to form an active enzyme (Kuciel et al.; 1990).

hPAP is secreted in high amounts into seminal fluid (Rönnberg et al.; 1981). Enzyme concentrations are often elevated in patients with prostate carcinomas and are correlated with tumour progression (Choe et al.; 1980, Griffiths 1980, Vihko et al.; 1980, 1981, and 1985). hPAP was a main diagnostic marker for prostate cancer until the arrival of the prostate-specific antigen.

As a large quantity of hPAP is present in human spermatic fluid, it has been suggested to have a physiological role in fertility (Coffey & Pienta 1987). Immunoreactive hPAP has been found in some non-prostate cells and tissues, such as leukocytes, kidney, spleen, placenta, pancreas, liver, stomach, granulocytes, neutrophils (Li et al.; 1980, Shaw et al.; 1981, Yam et al.; 1981, Aumüller & Seitz, 1985, Waheed et al.; 1985), anal gland and urethral gland of males (Kamoshida & Tsutsumi 1990), crypt epithelium of the duodenum (Drenckhahn et al.; 1987) and pancreatic islet cell carcinomas (Choe et al.; 1978). The serum levels of hPAP are very low in healthy individuals (0-5 ng/ml) (Cusan et al.; 1994), but are often elevated in malignant and benign prostatic disease (Choe et al.; 1980, Griffiths 1980, Vihko et al.; 1980, 1981, and 1985). As such, immunoassays for hPAP serum levels are useful in monitoring disease progression in prostate cancer.

It is assumed that SEVI peptides bind to viral or cellular membranes and activate processes that are essential for virus entry into the cell. The peptides, nucleic acids and antibodies of the invention are thus useful as therapeutics or diagnostics of viral infection, prostatic dysfunction, carcinoma or the susceptibility of a patient to a viral infection. The peptides, nucleic acids and antibodies of the invention are also useful to enhance infectivities of retroviral vectors that are used for gene delivery into cells or gene therapy approaches. They favour the infection of permissive target cells by retroviruses, e.g. HIV-1, HIV-2, SIV and other enveloped viruses like Ebola virus, Vesicular Stomatitis Virus (VSV), Mouse Leukemia Virus (MLV), and Hepatitis B Virus. The peptides of the invention exhibit dramatic enhancing effects on viral particle infectivity or fusion capability, such as the ability to favour HIV transmission to uninfected CD-4+ cells. Because of the high concentrations of hPAP and thus SEVI in human sperm, SEVI probably also facilitates HIV transmission from HIV seropositive individuals to healthy sex partners. The peptides of the invention may be used as markers for the probability of HIV-1 transmission during sexual intercourse.

The peptides are thus used for a broad range of therapeutic and diagnostic applications and are valuable laboratory tools for the performance and study of entry of viruses into cells.

A preferred embodiment of the invention is the use of SEVI peptides as general enhancers of viral infection or transduction efficiencies for routine laboratory practice or gene therapeutic approaches based on viral vector systems. The peptides are enhancing the entry of retroviral vectors designed for gene therapy into cells in vitro or in vivo. They may be administered in combination with a vector for gene therapy and mediate entry of the vector into the target cell. The peptides are also useful in vitro because they accelerate the uptake of viruses into cells. They are thus useful as a tool for studying viruses and their mechanisms of action.

Another embodiment of the invention is the use of SEVI peptides for diagnostic approaches, especially those of viruses like HIV-1. The virus particles are interacting with the SEVI peptides. They can thus be used to isolate viral particles from samples like serum, blood, plasma, sperm or tissues derived from HIV infected humans or SIV infected primates. One important issue in HIV-1 diagnostic is the reisolation of viruses directly from blood or cell samples derived from HIV-1 infected individuals. In the presence of SEVI, successful virus isolation could be favoured several times compared with routine diagnostic methods. Preferred methods are binding affinity assays and methods to remove viruses quantitatively from solutions suspected or known to comprise viruses in order to obtain safe solutions. In such methods, the peptides of the invention are preferably covalently bound to a support or a column.

The invention also relates to polynucleotides coding for the peptides according to the invention, such polynucleotides being preferably constituted of DNA, RNA, genomic DNA or PNA.

Another aspect of the invention relates to vectors containing the polynucleotide according to the invention, and genetically engineered host cells containing the vector according to the invention.

Recombinant or synthesized SEVI peptides can be used to enhance in general the entry of retroviral particles (oncoviruses, lentiviruses and Foamy viruses) and Hepatitis B and C Viruses into target cells. SEVI can also be used as a general enhancer of the infection/transduction rate of retroviral core particles that carry foreign envelope glycoproteins (pseudoparticles) like the G protein of the Vesicular Stomatitis Virus (VSV-G), the Env protein of MuLV, HBV HBsAg (Hepatitis B Virus surface antigen), Ebola Virus spike protein or envelope proteins from different HIV-1, HIV-2 and SIV variants. SEVI favours the infection rates of all analyzed retroviral particles, usually about 2 to 500 times. This allows to perform infection experiments, especially in primary cells, that have not been feasible before. The peptides of the invention are thus useful as laboratory tools in vitro.

Recombinant or synthesized SEVI peptides can also be used for diagnostic approaches i.e. isolation of HIV-1 or SIV from infected individuals. SEVI lowers the threshold for a detectable retroviral infection by at least 2 to 3 orders of magnitude. Thus, in the presence of SEVI, the sensitivity for a successful virus reisolation from patient samples is higher than without SEVI. SEVI lowers the detection limit in HIV diagnostics for the detection of replication competent HIV-1 from infected individuals. For example SEVI could allow a more efficient reisolation of virus from PBMC of HIV-1 infected individuals by cocultivation with indicator cells compared to samples without SEVI. SEVI also allows to efficiently reisolate virus from cell free samples of HIV-1 patients.

Recombinant or synthesized SEVI peptides can also be used to enhance gene delivery rates in ex vivo or in vivo gene therapy approaches based on retroviral vector systems. The generation of highly infectious retroviral vectors for gene therapy, especially for ex vivo gene therapy of stem cells, is a difficult procedure. The transduction efficiencies of retroviral vectors for stem cells are also low. In the presence of SEVI, however, stem cells and cell lines can be efficiently transduced with retroviral vectors, resulting in higher efficiencies for gene delivery into the target cell compared to samples containing no SEVI.

Expression vectors encoding SEVI and/or derivatives thereof can be used to transiently or stably transfect cell lines to produce recombinant SEVI peptides that can be purified from cell lysates or supernatants. Mono- or polyclonal antibodies specifically recognizing SEVI and/or derivatives can be used to measure SEVI concentrations in human sperm or seminal fluid as markers for prostatic cancer and the probability of HIV transmission. SEVI specific antibodies can also be used as medical compounds to neutralize SEVI activity in human sperm thus preventing HIV, HBV and HCV transmission by sexual intercourse.

The peptides according to the invention can be obtained by peptide synthesis, by a purification method from cells transfected with cDNA of peptide sequences or by a purification method starting from human sperm. In a preferred method, seminal fluid derived from sperm is subjected to cation exchange and reverse phase chromatography.

The peptides or antibodies according to the invention are preferably used in medicinal formulations. The medicinal formulation contains one or more of the peptides or antibodies according to the invention, or a physiologically acceptable salt of the peptides. Medicinal formulations can contain pharmaceutically usual auxiliary agents which contribute, for example, to the solubility, stability or sterility of the medicament or increase the efficiency of uptake into the body.

The form and composition of the medicament which contains the peptides or antibodies depends on the route of administration. Preferably, galenic formulations and application forms are selected in which the peptides or antibodies arrive at the target site in a non-degraded condition. The medicament can be administered locally as injection, drops, spray, tablets, suppositories, cream, ointments, gel etc. It is possible to perform the administration as a bolus or repeatedly over a period of time.

EXAMPLES

The peptides according to the invention were obtained by a purification method starting from human sperm (example 1). The peptides thus obtained were subjected to structural elucidation. The determination of the molecular masses of the purified peptides was effected by means of an electro spray mass spectrometer (ESI-MS). The sequence analysis of the native peptides was performed through Edman degradation with an ABI 473 sequencer (example 2 and 3). The peptide sequences according to the invention were also synthesized chemically, and the structure of the synthetically prepared peptide was also elucidated (examples 2 and 3). These synthetically prepared SEVI peptides form amyloid-like fibril structures either spontaneously or after incubation. These amyloid-like fibril structures dose dependently activate the infection of target cells with HIV-1, HIV-2, SIV's, VSV, MuLV and Ebola (examples 4-17).

The invention is demonstrated, first, by way of an example wherein a peptide fraction from a peptide library derived from human seminal fluid, favours HIV-1 infection of target cells in physiologically relevant concentrations (examples 1 and 16). Remarkably, SEVI peptides were most effective when the solution became turbid either spontaneously or after agitation with a precipitate being formed (Example 4). Examination of these precipitated SEVI peptides by reaction with Congo Red and subsequent microscopy (Example 5) using polarisized light and fluorescence microscopy indicated that precipitated SEVI peptides form fibrils. It was found that the precipitate contains the active peptide forms promoting viral infection (Example 4). It has been previously shown that β-amyloid fibrils associated with Alzheimer's disease enhance HIV-1 infection (Wojtowicz et al.; 2002). Indeed, electron microscopy confirmed that precipitated SEVI peptides consisted of typical fibrils (Example 4). It has been shown that self-assembly of amyloid proteins can be speeded up by seeding with preformed fibrils (Westermark; 2005). We also found that small proportions of active SEVI converted the "soluble and non-fibrilar" peptides into the active fibrils enhancing HIV-1 infection (Example 4). The invention is further demonstrated by examples wherein synthesized SEVI peptides dose dependently and non cytotoxically promote HIV-1 infection in primary cells and cell lines independently from coreceptor usage or HIV-1 subtype (example 4, 6-17). Besides, it was shown that SEVI dramatically enhances infection of HIV-1 by 2 to 3 orders of magnitude by a direct interaction with the viral particle and the cell (example 14 and 15). The invention is further demonstrated by way of examples wherein SEVI also favoured infection of target cells with other lentiviral vectors than HIV-1, i.e. Simian Immunodeficiency viruses and oncoretroviruses MuLV (Mouse Leukemia Virus) (example 17). SEVI also increased infection rates of VSV-G pseudotyped particles, indicating that SEVI enhances viral transductions rates und is thus a useful tool for improving gene therapy approaches based on retroviral vector systems. Since SEVI lowers the threshold to detect HIV-1 infection by 3-4 orders of magnitude, SEVI can also be a valuable tool for viral diagnostics, especially the isolation of HIV-1 from HIV-1 infected individuals for geno- and phenotypic resistance testing.

SEVI peptides could be isolated from human seminal fluid by chromatographic methods and using an HIV-1 cell infection assay. The biochemical characterization of the peptides according to the invention was performed by mass spectrometry and the complete sequence analysis of all amino acids.

The invention is further described by means of the following examples.

Example 1

Isolation of the HIV-1 Infection Promoting SEVI Peptides

Purification from Human Sperm

For the generation of a peptide library derived from human seminal plasma, 283 ml human sperm was collected from different healthy donors (n>50). For collection of sperm, healthy volunteers ejaculated whole sperm into a 50-100 ml plastic tube and the sperm was stored at −20° C. immediately after ejaculation. For preparation of proteins and peptides the spermatozoa and seminal plasma were separated by centrifugation of the defrozen sperm at 17,000×g (9600 rpm) at 4° C., and the supernatant containing seminal plasma (sn A) was stored at 4° C. Next, the pellet was rinsed two times with ice cold extraction buffer (1 M acetic acid, 20 mM ascorbic acid, 1 mM EDTA, 2 M sodium chloride, pH 2.0; 10 min at 17,000 g) and supernatants B and C were pooled with supernatant A. Pooled supernatants A-C (380 ml) were diluted with extraction buffer to 760 ml and then diluted to 5 L with diafiltration (DF) buffer (0.1 M acetic acid, 2 mM ascorbic acid, 0.1 mM EDTA; pH 3.0) using a polysulfon membrane with a molecular cut-off of 50 kDa (Sartocon ultrasart SM 146501E-SG; Sartorius, Göttingen, Germany). This solution was reconcentrated to 0.5 l in 65 min, diluted to 1 L with DF buffer and then diafiltrated with DF buffer to 9.5 L permeate in 60 min. The permeate contained all proteins and peptides <50 kDa and was further processed by a first chromatographic separation step.

Cation Exchange Chromatography:

For a first separation, a cation exchange column (Fractogel TSK SP 650 (S), Merck, Darmstadt, Germany; 20-50 microm particle size; 860 ml column volume) was equilibrated with water, pH 2.5 after conditioning with 0.5 M NaOH and 0.5 M HCl. The permeate was diluted with water to a volume of 22 L and the pH was adjusted with HCl to 2.5, the conductivity was 4.93 mS/cm. The conditioned permeate was then loaded on the cation exchange column (flow rate: 20 ml/min). After washing with 29 L water, pH 2.5, the peptides/proteins were eluted using the following buffers (FIG. 1A):

1. 0.1 M citric acid, pH 3.6, volume: 4.4 L
2. 0.1 M acetic acid+0.1 M sodium acetate, pH 4.5, volume: 1.5 L
3. 0.1 M malic acid, pH 5.0, volume: 2.2 L
4. 0.1 M malonic acid, pH 5.6, volume: 1.5 L
5. 0.1 M $NaH_2PO_4$, pH 6.6, volume: 1.2 L
6. 0.1 M $Na_2HPO_4$, pH 7.4, volume: 1.5 L
7. 1 M ammonium acetate, pH 7.0, volume: 1.8 L
8. water, pH 7.0, volume: 1.5 L
9. 0.1 M NaOH, pH 13, volume: 3.0 L The eluates obtained with buffers 1-6 resulted in eluates numbered 1-6. The eluates 7-9 were pooled and the pooled eluate was termed eluate number 7.

First Reverse Phase Chromatography:

The second separation was carried out on a reverse phase (RP) chromatography column (C18, 47×300 mm i.d., 10-20 microm particle size, 30 nm pore size, Vydac, Hesperia, Calif., USA) (exemplarily shown for eluate 7 in FIG. 1B). Each eluate 1 to 7 was applied to the RP C18 column and the separation was carried out in seven different runs and the peptides were eluated in gradient elution under identical conditions:

Flow rate: 40 ml/min
Buffer A: 10 mM HCl
Buffer B: A+800% (v/v) acetonitrile
Gradient elution: from 1000% A to 60% B in 47.5 min
from 600% B to 1000% B in 2.5 min Fractions of 50 ml were collected and each run resulted in 40 peptide containing fractions. In total 280 fractions were obtained and from each fraction an aliquot corresponding to 1.4 ml equivalent of seminal plasma (0.25 ml fraction volume) was taken and immediately lyophilized. The original fractions were immediately stored at −20 C. prior to further chromatographic separation.

Figure 2:
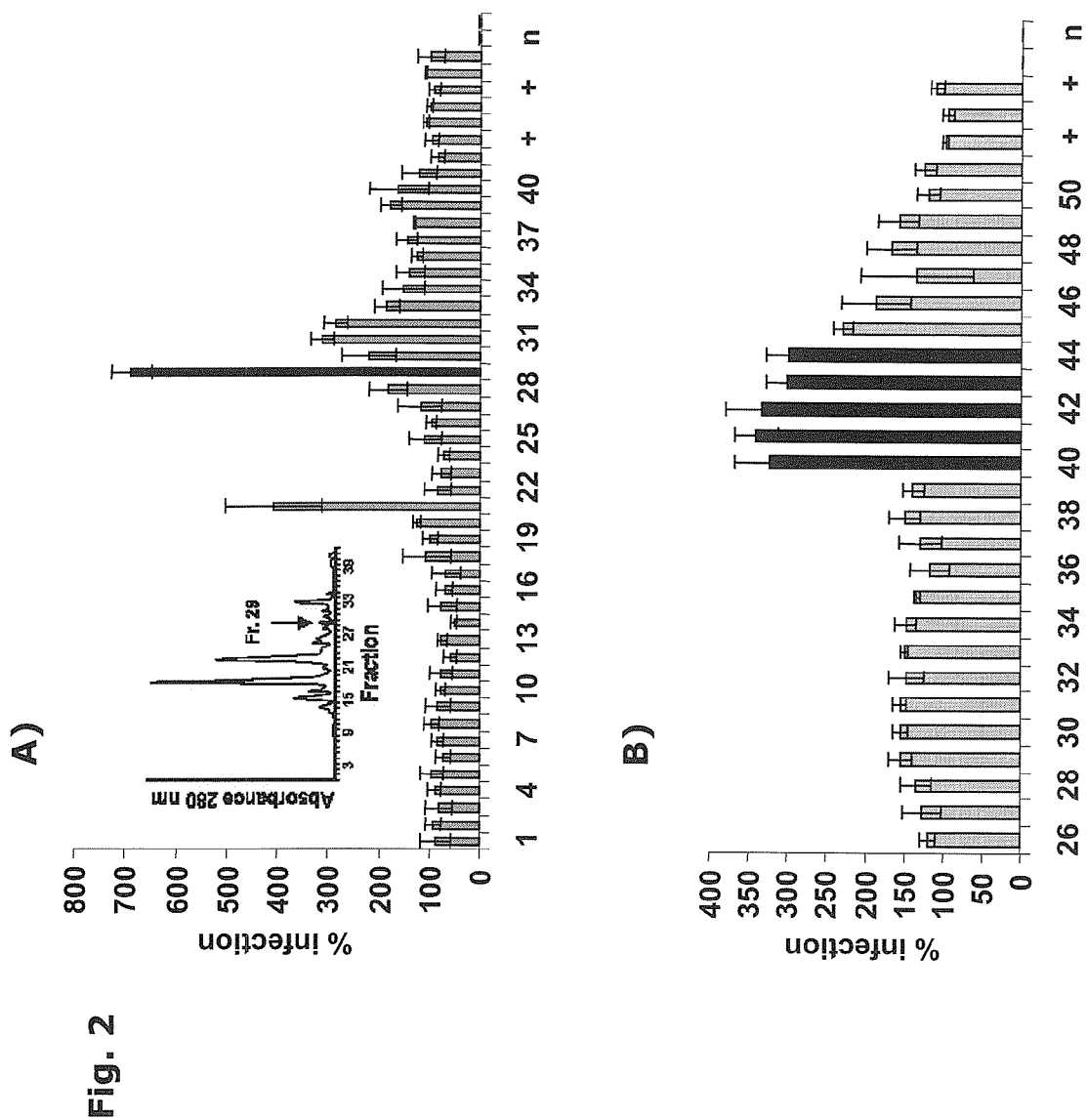

Testing of the Fractions:

The lyophilized peptide fractions from pH pool 7 containing 1.4 ml sperm equivalent/ml were reconstituted in 33 µl of FBS (foetal bovine serum; Invitrogen; #10270-106) free D-MEM (Invitrogen, #41965-039) containing 100 units/ml penicillin G and 100 µg/ml Streptomycin sulphate (Pen/Strep) (Invitrogen, #15140-163). 4000 P4-CCR5 cells (Charneau et al.; 1994.) were sown out in 96 well flat bottom plates (Greiner; #655180) in a total volume of 100 µl in DMEM (100% FBS, Pen/Strep). P4-CCR5 cells express HIV-1 receptors CD4, CCR5 and CXCR4 and stably contain a LTR-lacZ construct. After successful infection of these cells with HIV-1, the virally encoded Tat protein is expressed, which transactivates viral gene expression via binding to the LTR (Charneau et al.; 1994). Thus Tat also activates the expression of the cell encoded LTR-lacZ, resulting in the production of the enzyme β-galactosidase in infected cells. The activity of the enzyme is directly proportional to viral infectivities. The next day, medium was removed, 30 μl of fresh medium and 10 μl of dissolved peptide fractions were added. After 4 h incubation at 37° C., 10 μl of the HIV-1 NL4-3 stock (Adachi et al.; 1986) was added to the cells. HIV-1 NL4-3 was derived by transient transfection of 293T cells with proviral DNA using the calcium phosphate method (BD Biosciences; CalPhos Mammalian Transfection Kit; #631312). HIV-1 stocks were stored at −80° C. 3 days post infection viral infection was detected using the β-Gal Screen Kit from Tropix (Biosystem; #T1027). The supernatant of cells was discarded and 40 μl of an 1:1 diluted β-Gal Screen solution containing the β-Gal substrate and PBS was added. After 30 min incubation, 35 μl of lysed cellular extracts were pipetted in 96 well lumiplates (Nunc; #136101) and chemiluminescence was detected using a luminometer (OrionII, Berthold detection systems). β-galactosidase activities were obtained as relative light units per second (RLU/s). Values obtained in positive controls (infected cells containing no peptide) were set to 1000% and all other values were calculated by dividing the absolute RLU/s in the presence of peptide by the median values obtained from cells containing no peptide×100. In the presence of fr. 29 from pH pool 7, reporter gene activities were increased more than 6.8 fold compared to infected control cells containing no peptide (FIG. 2a). These results demonstrate for the first time, that seminal fluid contains compound(s) that have favourable effects on HIV-1 infection. The presence of an HIV-1 activating peptide in human sperm is an important finding, since HIV-1 transmission in the human population preferentially occurs via sexual contact between HIV-1 infected and healthy sex partners.

To isolate the HIV-1 activating peptide, fractions 29-31 were further purified using chromatographic techniques.

Second Reverse Phase Chromatography:

The third separation step was carried out on a reverse phase (RP) chromatography column (C18, 20×250 mm i.d., 5 microm particle size, 30 nm pore size, Vydac, Hesperia, Calif., USA) (FIG. 1C). The fractions 29-31 from pool 7 were applied to the RP C18 column and the peptides were eluated in gradient elution using following conditions:

Flow rate: 7 ml/min
Buffer A: 0.1% TFA
Buffer B: A+80% (v/v) acetonitrile
Gradient elution: from 10% A to 50% B in 50 min
from 60% B to 100% B in 1 min A total of 60 fractions of 7 ml were collected and aliquots of 0.5% (35 microL) were lyophilized.

Aliquots corresponding to 1.4 ml sperm equivalent of the chromatography 030718-1 (0.5% of the fraction) were then analyzed in the virus inhibition assay exactly as described above. In the presence of peptide fractions 40 to 44 viral infectivities were increased 3 to 4 times compared to control cells (FIG. 1D and FIG. 2B).

Example 2

Biochemical Analysis of HIV Infection-Activating Peptides

Mass analysis of purified peptides and fractions was performed with Voyager De MALDI-TOF-MS (Applied Biosystems, Darmstadt, Germany) using standard conditions as recommended by the manufacturer. Mass determination of the purified peptides was additionally carried out on a Sciex API III quadrupol mass spectrometer (Sciex, Perkin-Elmer) with an electrospray interface (ESI-MS; see FIG. 1D). Peptides were sequenced on an 473 A gas-phase sequencer (Applied Biosystems, Weiterstadt, Germany) by Edman degradation with on-line detection of phenylthiohydantoin amino acids using the standard protocol recommended by the manufacturer. A database alignment (Swiss-Prot database) of the obtained sequences showed 100% sequence identity to the precursor of human prostatic acid phosphatase (hPAP; accession number P15309), amino acid residues 247-286 of the hPAP precursor sequence (the numbering refers to the amino acids including the pro-sequence).

The following fragments of PAP were detected in human seminal plasma by mass and/or sequence determinations:

```
Seq ID No. 1: PAP (247-286)
YGIHKQKEKSRLQGGVLVNEILNHMKRATQIPSYKKLIMY
(Mr theor. 4714.6 Mr detected 4715.3)

Seq ID No. 2: PAP (248-286)
GIHKQKEKSRLQGGVLVNEILNHMKRATQIPSYKKLIMY
(dominant peptide)
(Mr theor. 4551.4 Mr detected 4551.8)

Seq ID No. 3: PAP (249-286)
IHKQKEKSRLQGGVLVNEILNHMKRATQIPSYKKLIMY
(Mr theor. 4494.4) Mr detected 4507)

Seq ID No. 4: PAP (250-286)
HKQKEKSRLQGGVLVNEILNHMKRATQIPSYKKLIMY
(Mr theor. 4381.2) Mr detected 4388)

Seq. ID No. 5 PAP (251-286)
KQKEKSRLQGGVLVNEILNHMKRATQIPSYKKLIMY
(Mr detected 4244.1)

Seq. ID No. 6 PAP (252-286)
QKEKSRLQGGVLVNEILNHMKRATQIPSYKKLIMY
(Mr detected 4115.9)

Seq. ID No. 7 PAP (253-286)
KEKSRLQGGVLVNEILNHMKRATQIPSYKKLIMY
(Mr detected. 3987.8)

Seq ID No. 8: PAP (248-285)
GIHKQKEKSRLQGGVLVNEILNHMKRATQIPSYKKLIM ...
(Mr theor. 4388.3 Mr detected 4386.2)

Seq ID No. 9: PAP (248-284)
GIHKQKEKSRLQGGVLVNEILNHMKRATQIPSYKKLI ...
(Mr theor. 4257.1 Mr detected 4254.3)

Seq ID No. 10: PAP (248-283)
GIHKQKEKSRLQGGVLVNEILNHMKRATQIPSYKKL ...
(Mr theor. 4143.9 Mr detected 4141.9)

Seq ID No. 11: PAP (248-282)
GIHKQKEKSRLQGGVLVNEILNHMKRATQIPSYKK ...
(Mr theor. 4030.7 Mr detected 4028.3)

Seq ID No. 12: PAP (247-282)
YGIHKQKEKSRLQGGVLVNEILNHMKRATQIPSYKK ...
(Mr theor. 4193.9 Mr detected 193.3)
```

Example 3

Chemical synthesis of selected, linear PAP/SEVI peptides in mg-amounts was carried out using conventional Fmoc chemistry. The synthesized peptides were purified using analytical reverse phase chromatography and their purity and identity were analyzed by mass and sequence determinations by the methods and equipments described above.

Example 4

Amyloid Like Fibrils in Activated Pap Solutions Enhance HIV Infection

CEMX174 5.25 M7 cells, kindly provided by Nathaniel Landau, were cultivated in RPMI 1640 (Invitrogen; #21875, 034) containing 10% FBS and Pen/Strep. CEMX174 5.25 M7 cells contain LTR-luc (Firefly-luciferase) and LTR-GFP (green fluorescence protein) constructs stably integrated into the chromosomal DNA. After productive infection of CEMX174 5.25 M7 cells with HIV-1, HIV-2 or SIV, the viral transactivator protein Tat is expressed and transactivates the expression of Luc and GFP via interaction with the LTR. Thus HIV-1 infection can be detected by measuring luciferase activities in cellular lysates or GFP expression in living cells. HIV-1 stocks were generated by transient transfection of 293T cells with proviral DNA (see example 1). One day post transfection medium was removed and fresh DMEM (100% FBS) was added. Viral particles containing supernatants were harvested 30 h later and virus concentrations were measured using a p24 antigen ELISA (NIH reagent program).

In initial experiments the activity of SEVI in enhancing HIV-1 infection varied considerably. It was noted that the peptide was most effective when the solution became turbid either spontaneously or after agitation and that the turbidity of SEVI solutions correlated with the efficiency in enhancing HIV infection. To elucidate the nature of the turbid components of activated SEVI solutions, PAP(248-286) at a concentration of 5 mg/ml in phosphate buffered saline was incubated by shaking at 1000 rpm. After overnight incubation at 37 degrees Celsius the peptide solution became turbid and fibril-like structures were visible. To analyze whether the unsoluble, fibrilar or the soluble portion of this preparation of SEVI peptides activates HIV-1 infection, fibril-like structures were separated by centrifugation at 10000 g for 5 min, the supernatant was collected and the pellet redissolved in the same amount of PBS. To analyze the effect of these solutions on HIV infection, dilutions were prepared in 96 well plates using FBS free DMEM. Next, 50,000 CEMX174 5.25 M7 cells were sown out in a total volume of 50 µl (RPMI 1640, 100% FBS) in a 96 well flat bottom plate, 10 µl of peptide dilutions were added and infection was subsequently performed using 1 ng of p24 antigen of HIV-1 NL4-3 in a volume of 40 µl (total volume 100 µl). After 2 days incubation at 37° C., virus infection was determined by measuring luciferase activities in cellular lysates using the luciferase assay system (Promega; #E1501). Briefly, cells were resuspended, transferred to 96 well V shaped plates (Greiner; #651180), and centrifuged for 5 min at 1200 rpm. Cell supernatant was removed and remaining cell pellets were lysed in 30 µl 1× luciferase lysis buffer (Promega; #E1531). After transfer of 20 µl of the lysates to 96 well lumiplates (Nunc; #136101), 100 µl of luciferase reagent (Promega) was added and chemiluminescence was detected using a luminometer (see example 1), detecting luciferase activities as relative light units per second (RLU/s). Average values of infectivity derived from triplicate infections are shown relative to those measured in the absence of peptides (1000%). Results shown in FIG. 3A demonstrate that only the active turbid SEVI stock solution and the redissolved pellet, containing the fibril-like structures, dose dependently enhanced HIV-1 infection, whereas the clear supernatant showed no effect. Hence, only the precipitable part contains the active, HIV-1 enhancing forms.

Figure 3:
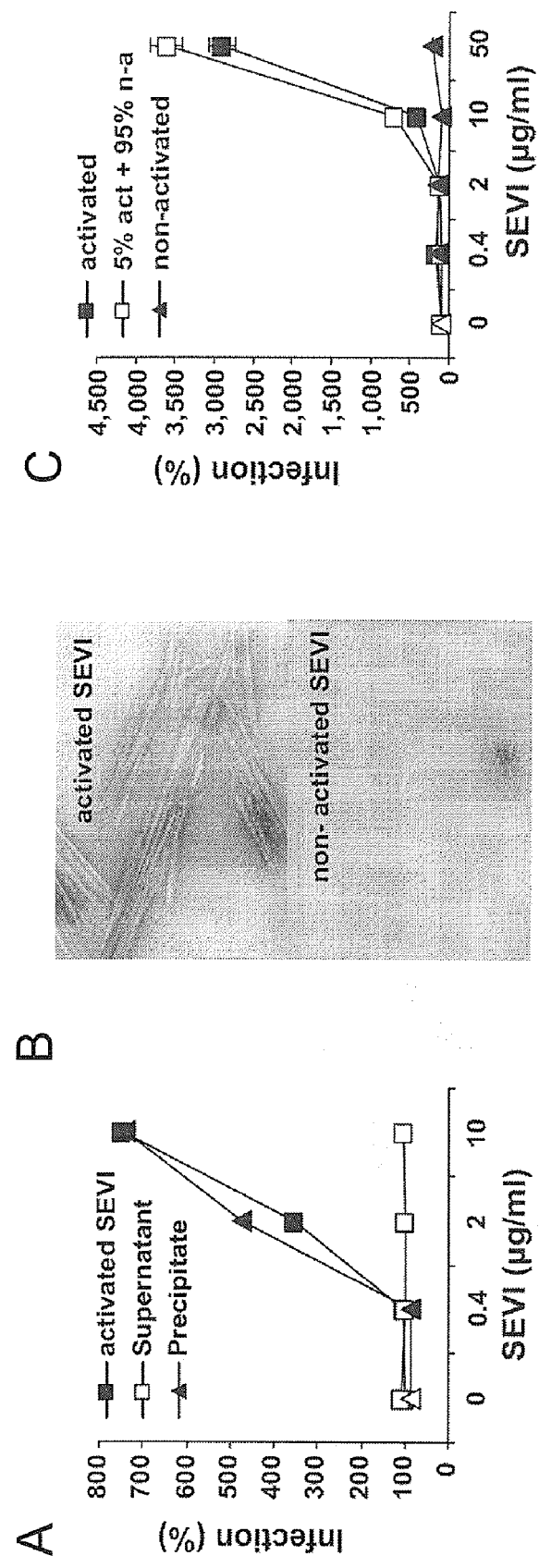

It has been previously shown that β-amyloid fibrils associated with Alzheimer's disease enhance HIV infection (Wojtowicz at al., 2002). To figure out if turbid SEVI solutions also contain β-amyloid-like fibrils electron microscopy was performed. Electron micrographs shown in FIG. 3B revealed that a turbid, HIV-activating solution contains β-amyloid-like fibrils, whereas no fibrils could be detected within the clear supernatant or a non-activated solutions (FIG. 3B, and data not shown).

It has been shown that self-assembly of amyloid peptides can be accelerated by seeding with preformed fibrils (Westermark et al., 2005). It was also found that a small proportion of activated fibril-containing PAP(248-286) converted an unassembled PAP(248-286) solution into the active fibrils enhancing HIV-1 infection (FIG. 3C).

Example 5

Detection of β-Amyloid Fibrils in Active SEVI Solutions

Figure 4:
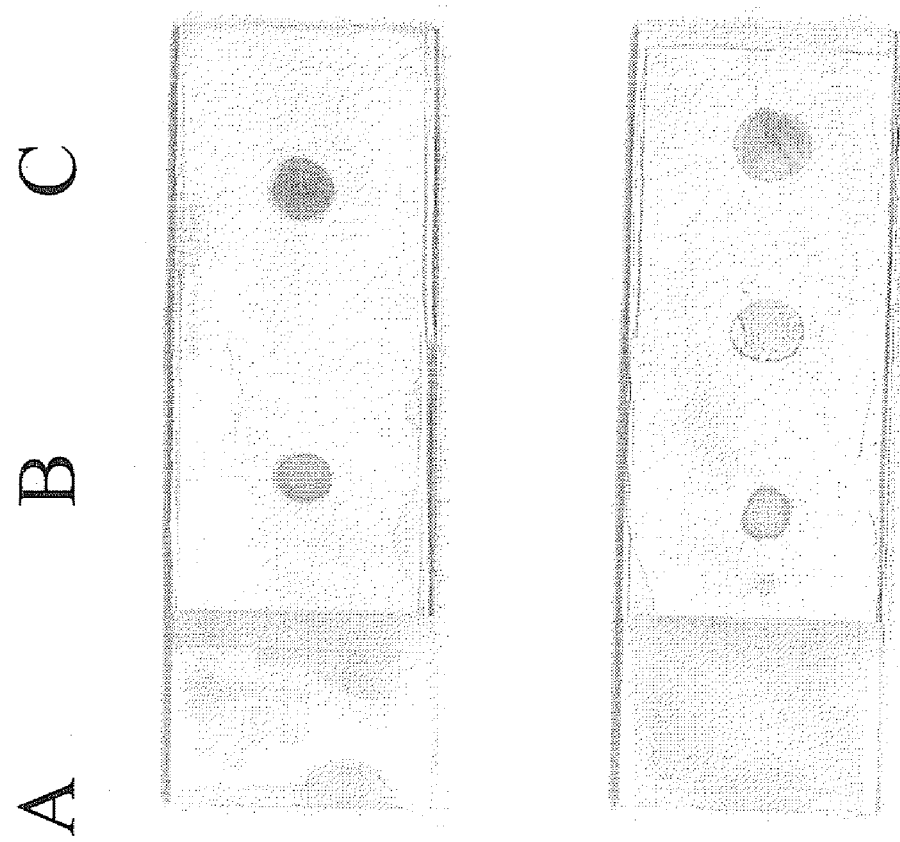
Figure 5:
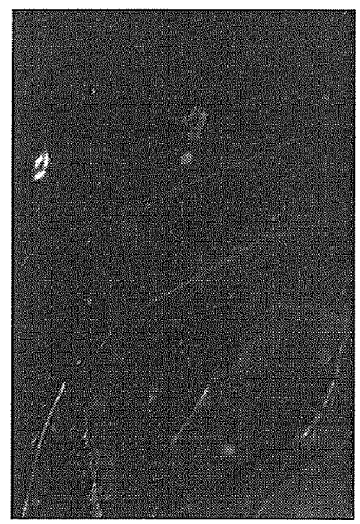
Figure 5:
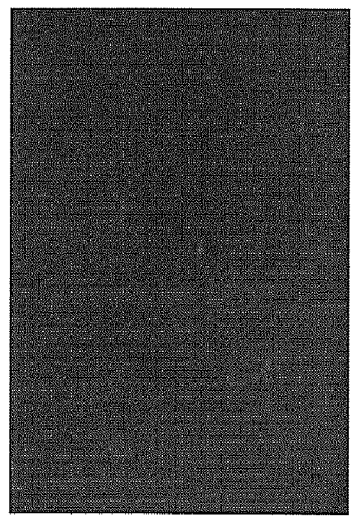
Figure 5:
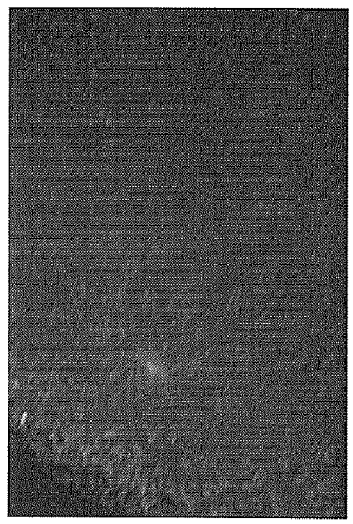
Figure 6:
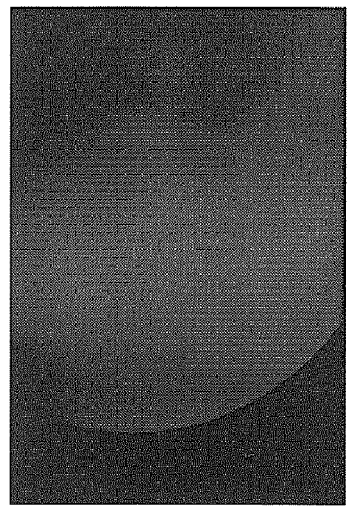
Figure 6:
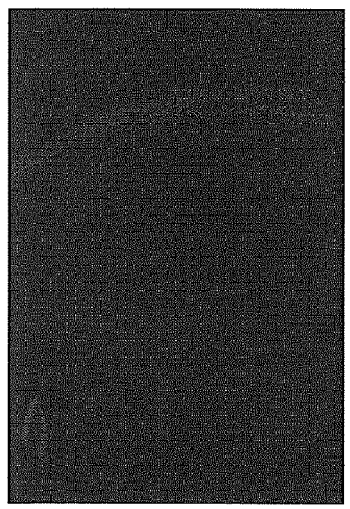
Figure 6:
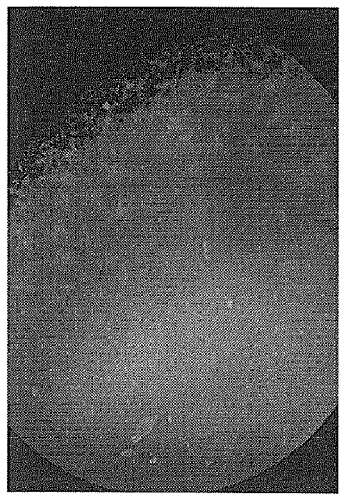

PAP(248-286) at a concentration of 5 mg/ml in phosphate buffered saline was incubated by shaking at 1000 rpm overnight at 37 degrees Celsius. A few drops of the resulting activated turbid oligopeptide solution were transferred to a polylysine-coated slide and the protein solution was dried under airflow in an extractor hood. The dried protein was stained with saturated Congo red solution (in 80% ethanol and 2 M NaCl) and washed with 80% ethanol. As reference proteins and peptides, solutions of soluble, non incubated PAP(248-286) and human albumine in similar concentrations were transferred to the same slides and stained equally. Whereas the activated PAP(248-286) peptide showed the typical Congo Red staining (FIG. 4, upper panel), the non-activated peptides did not or marginally react with Congo Red (FIG. 4, lower panel) and the albumine control showed a blue coloration (FIG. 4). The same slides stained with Congo red were examined by light and fluorescence microscopy. Conventional light microscopy using polarized light showed the typical birefringence (double refraction) effect of activated PAP(248-286) (FIG. 5A), whereas the non-activated SEVI peptide (FIG. 5B) and the albumine control (FIG. 5C) did not show a birefringence effect. Staining with Congo Red and birefringence are typical criteria for fibril formation (Nilsson; 2004). In addition, by conventional fluorescence microscopy remarkable differences in colour and intensity of the SEVI fibrils (lucent orange, FIG. 6A) could be observed, in contrast to the soluble, non-activated PAP(248-286) (black, FIG. 6B) or albumine (green, FIG. 6C). The differences observed between activated, fibril-containing and non activated, clear PAP(258-286) solutions using Congo Red staining and light, fluorescence or EM microscopy, clearly show that SEVI solutions contain β-amyloid like fibrils, which are prerequisite to activate and favour HIV infection.

Example 6

Determination of the HIV-1 Enhancing Effect of Different SEVI Peptides on HIV-1 Infection To analyze the effect of synthesized SEVI peptides on HIV infection, samples were resuspended in FBS free DMEM to yield a stock solution of 5 mg/ml and shacked for 20 h at 37° C. at 1400 rpm (rotations per minute) resulting in a turbid solution. Peptide dilutions were prepared in 96 well plates using FBS free DMEM. Next, 5000 CEMX174 5.25 M7 cells were sown out in a total volume of 50 µl (RPMI 1640, 100% FBS) in a 96 well flat bottom plate, 10 µl of peptide dilutions were added and infection was subsequently performed using 30 pg of p24 antigen of HIV-1 NL4-3 in a volume of 40 µl (total volume 100 µl). After 20 hours incubation at 37° C., virus infection was determined by measuring luciferase activities in cellular lysates using the luciferase assay system (Promega; #E1501). Briefly, cells were resuspended, transferred to 96 well V shaped plates (Greiner; #651180), and centrifuged for 5 min at 1200 rpm. Cell supernatant was removed and remaining cell pellets were lysed in 30 µl 1× luciferase lysis buffer (Promega; #E1531). After transfer of 20 µl of the lysates to 96 well lumiplates (Nunc; #136101) 100 µl of luciferase reagent (Promega) was added and chemiluminescence was detected using a luminometer (see above), detecting luciferase activities as relative light units per second (RLU/s). Average values of infectivity derived from triplicate infections are shown relative to those measured in the absence of peptides (1000%).

Figure 7:
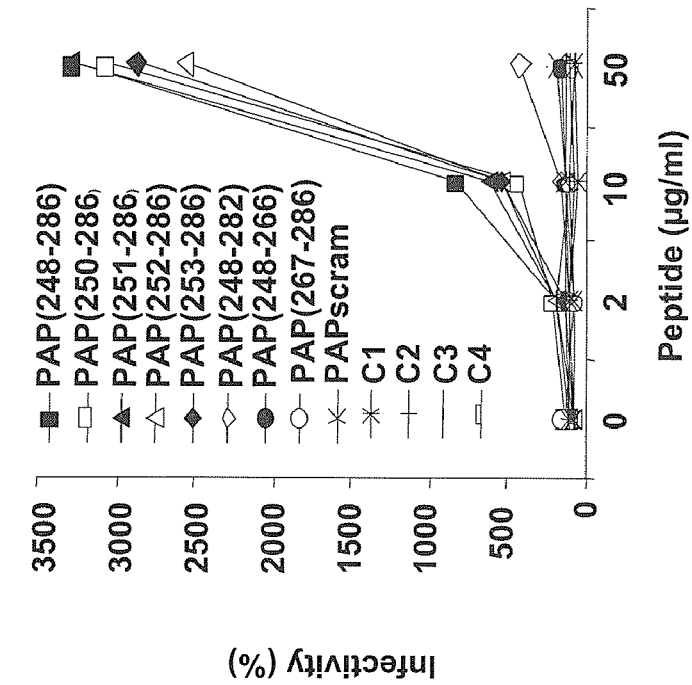

All peptides indicated in FIG. 7B were dissolved and incubated under the same conditions. PAP fragments (248-286), PAP(250-286), PAP(251-286), PAP(252-286) and PAP(253-286) dose dependently enhanced HIV-1 infection. In the presence of 50 µg/ml peptide, luciferase activities were increased about 30 fold compared to those from control cells containing no SEVI (FIG. 7A). In contrast, a "scrambled peptide" (PAP-scram, consisting of the same amino acids as a SEVI peptide but with a random distribution within the amino acid sequence), control peptides c1-c3 as well as C- and N-terminal fragments [PAP(248-266) and PAP(267-286)] had no enhancing effect on HIV-1 infection (FIG. 7A). This data indicate that enhancing effect of SEVI on HIV-1 infection is specific.

Example 7

The Promoting Effect of SEVI on HIV-1 is Cell Type Independent

Figure 8:
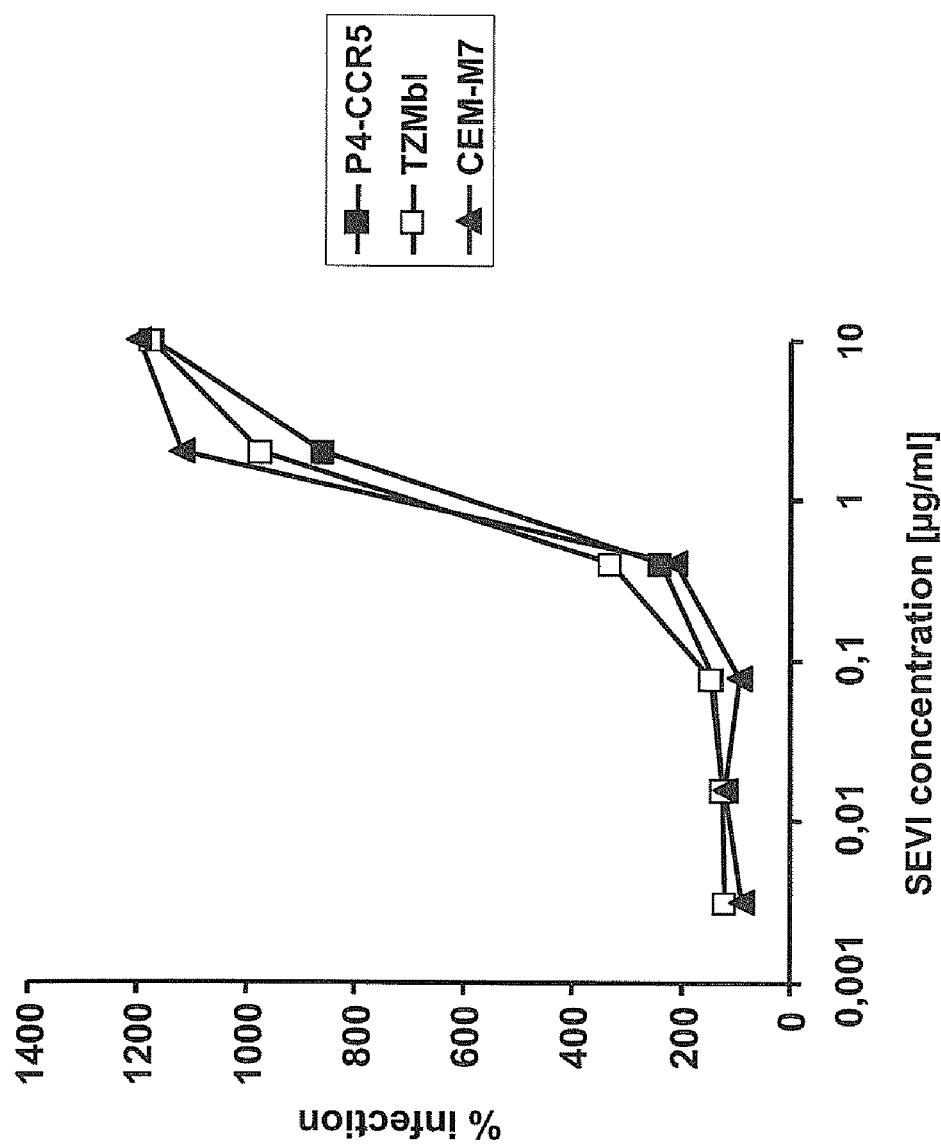
Figure 11:
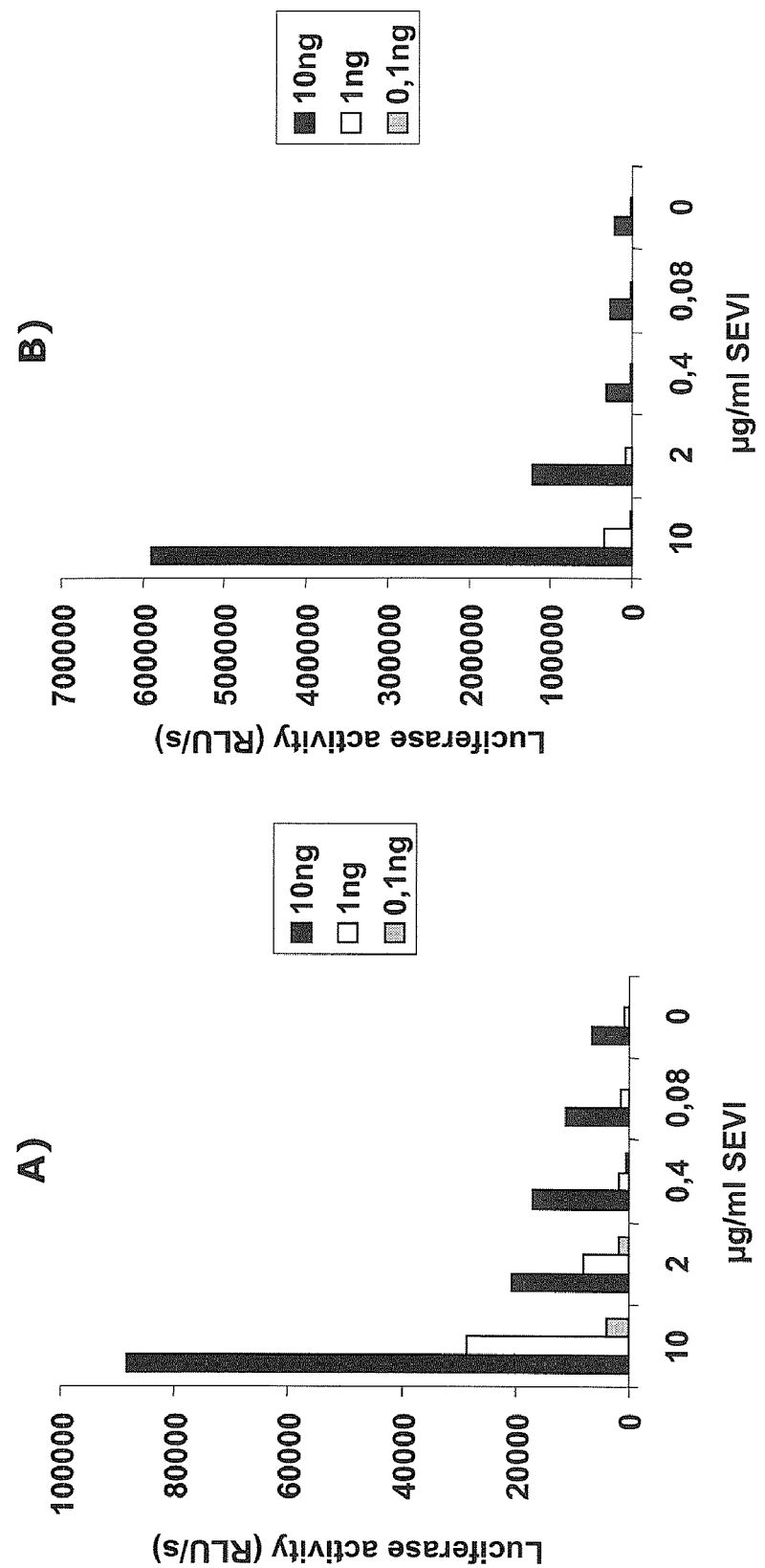
Figure 12:
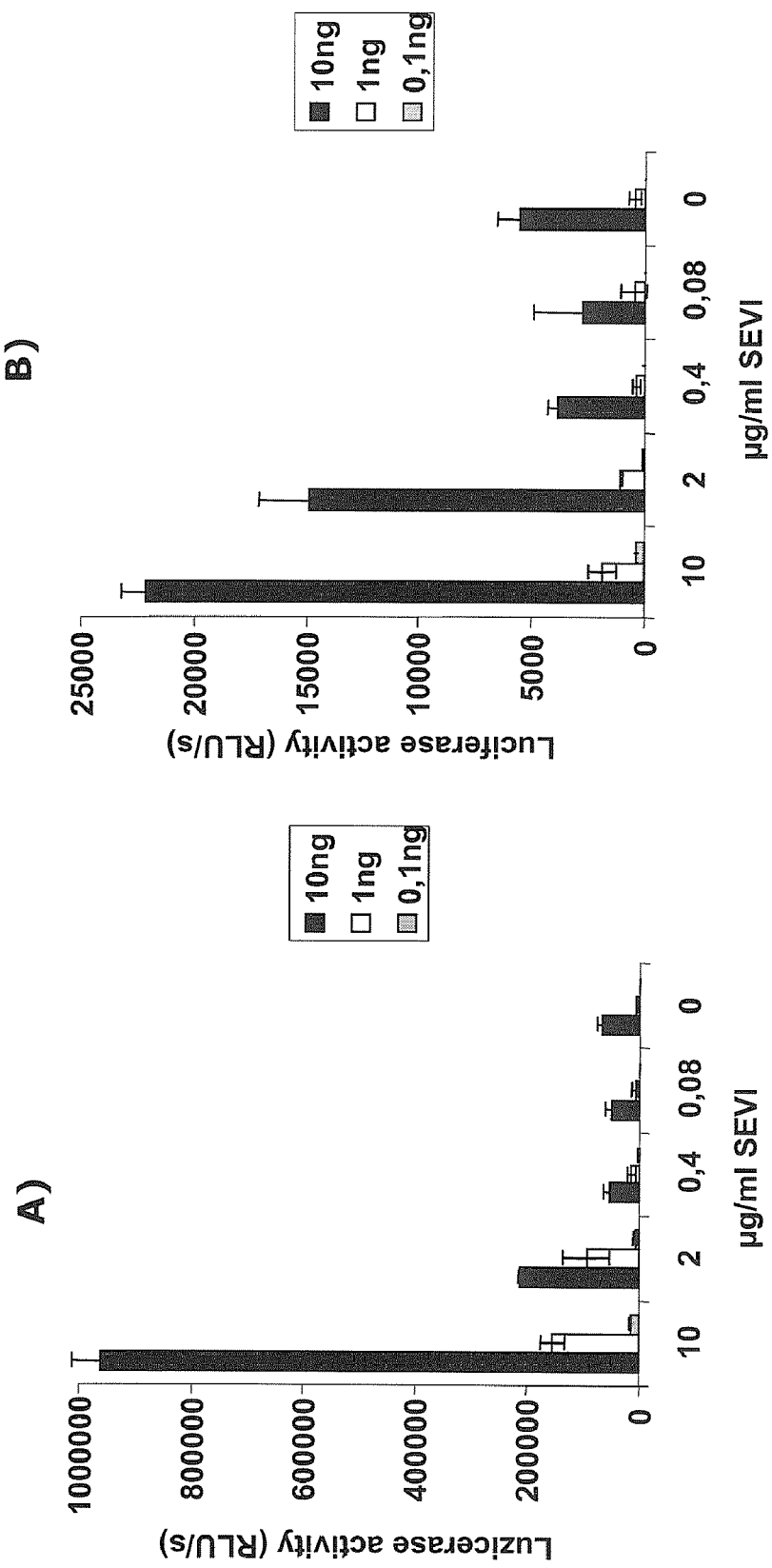

To analyze whether the enhancing effect on HIV-1 infection depends on the cell type used, 2000 adherent TZM-bl (Wei et al.; 2002) or P4-CCR5 and 5000 CEMX174 5.25 M7 suspension cells were sown out in a volume of 50 µl. The day after, 10 µl SEVI [fibrilar PAP(250-286)] dilutions were added and cells were infected with 1 ng p24 antigen of HIV-1 NL4-3 in a total volume of 100 µl. 2 days post infection viral infectivity in TZM-bl or P4-CCR5 cells was detected using the Gal Screen Kit. Briefly, supernatants were removed and 40 µl of a 1:1 dilution of Gal Screen in PBS was added to the cells. Gal Screen contains the β-Galactosidase substrate and components to lyse the cells. After 30 min incubation at RT, 30 µl of cell lysates were transferred to 96 well lumiplates and chemiluminescence was detected using a luminometer. SEVI dose dependently promoted HIV-1 infection in adherent (TZM-bl and P4-CCR5) and suspension cells (CEMX174 5.25 M7) (FIG. 8). In the presence of 0.4 µg/ml SEVI, HIV infection was enhanced by the factor of 2.1 in CEMX174 5.25 M7 cells, 2.4 in P4-CCR5 and 3.3 in TZM-bl cells compared to infection rates obtained in controls without peptide. At the highest concentration analyzed (10 µg/ml), HIV infection of all three cell types was increased more than 10 fold. Similar results were also obtained in human PBMC and macrophages (FIGS. 11 and 12). These data indicate that the promoting effect of SEVI on HIV-1 infection is independent of the cell type used.

Example 8

SEVI has no Effect on Cell Viability or Endogenous LTR Activity

Figure 9:
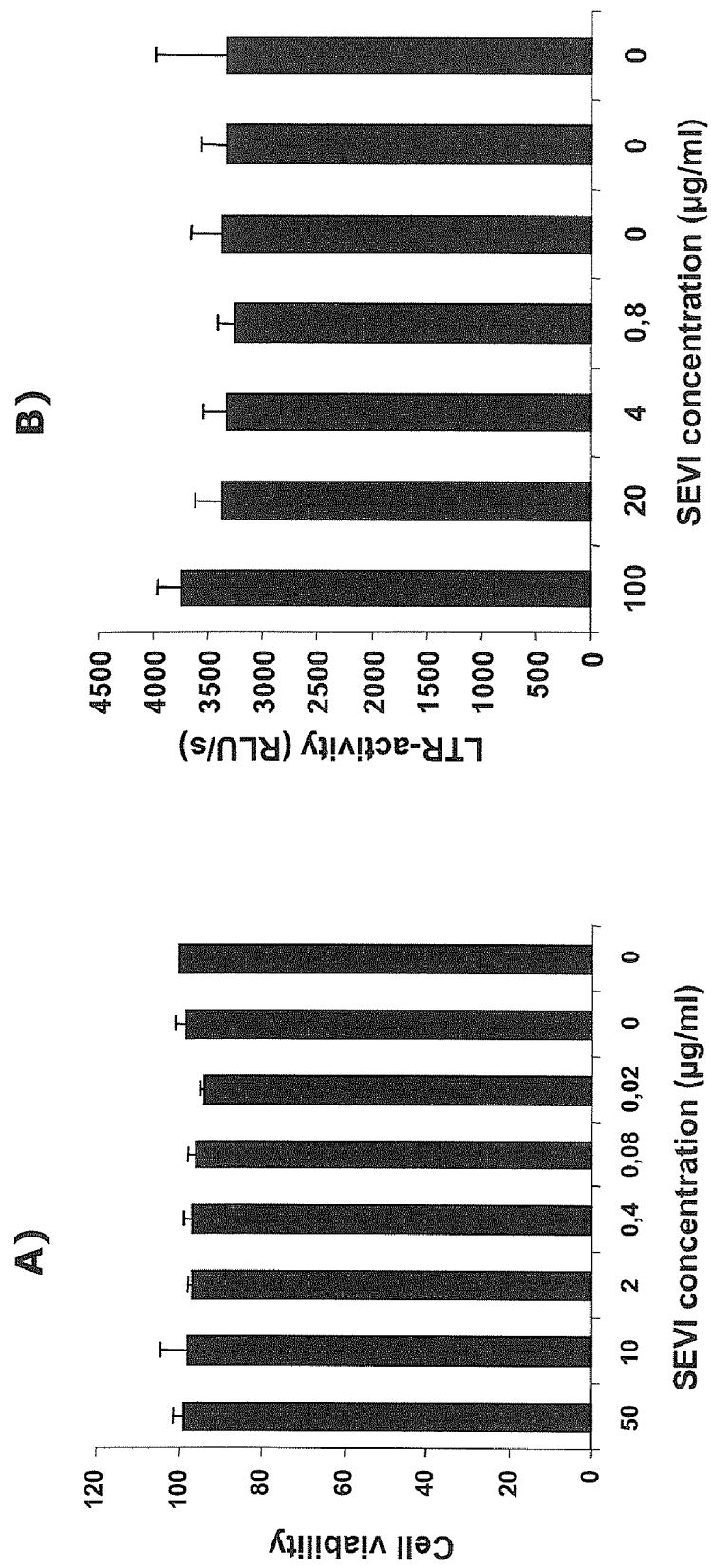

To analyze whether SEVI exerts cytotoxic effects on cells or stimulates cell proliferation, 4000 TZM-bl cells were sown out in a volume of 100 µl in 96 well flat bottom plates. The day after medium was replaced by 90 µl of fresh medium and SEVI [fibrilar PAP(250-286)] dilutions were added to a final volume of 100 µl. After 3 days 10 µl of a 5 mg/ml MTT (Sigma; # M2128) solution was added and cells were incubated for 4 h at 37° C. In living cells mitochondrial dehydrogenases oxidize the yellow MTT salt to blue formazan crystals (Schiff et al.; 1985). After dissolving the crystals in 1:1 Ethanol/DMSO, samples containing living cells appear blue whereas samples from dead cells are clear. Optical density (OD) was measured at 560/650 nm using a photometer (Molecular Devices). As shown in FIG. 9A, cell viability in samples containing high concentrations of SEVI was not affected by the peptide indicating that the peptide neither exerted cytotoxic effects nor induced cellular proliferation.

It could be possible, that SEVI does not enhance HIV-1 infection but instead activates the cell encoded LTR driving the expression of luc or lacZ in CEMX174 5.25 M7 or TZM-bl/P4-CCR5 cells, respectively. To analyze this, TZM-bl cells were incubated with different concentrations of SEVI without infection, and endogenous LTR activity was measured 3 dpi using the Gal-Screen kit. LTR activities were equal in all samples analyzed, demonstrating that SEVI indeed enhances HIV-1 infection and does not increase endogenous LTR activity in the reporter cells used (FIG. 9B).

Example 9

Figure 10:
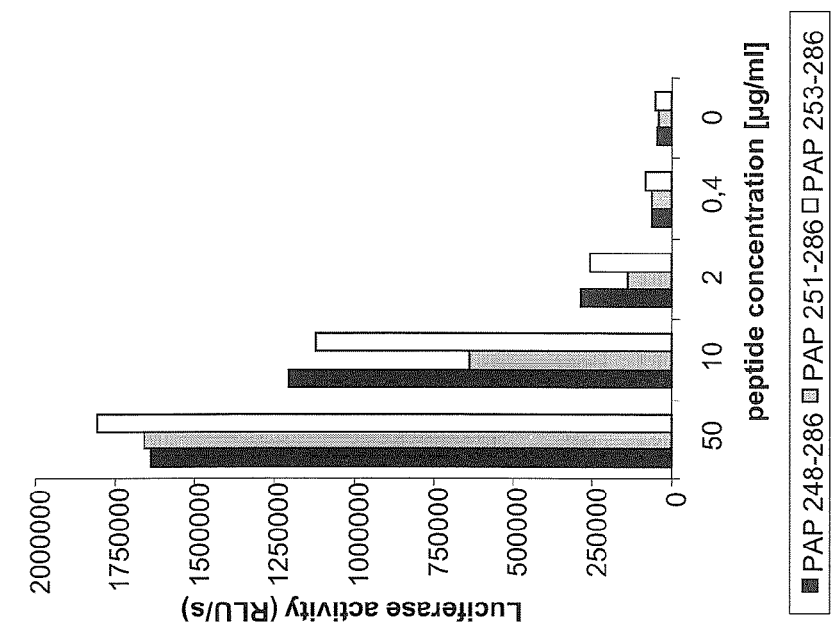
Figure 10:
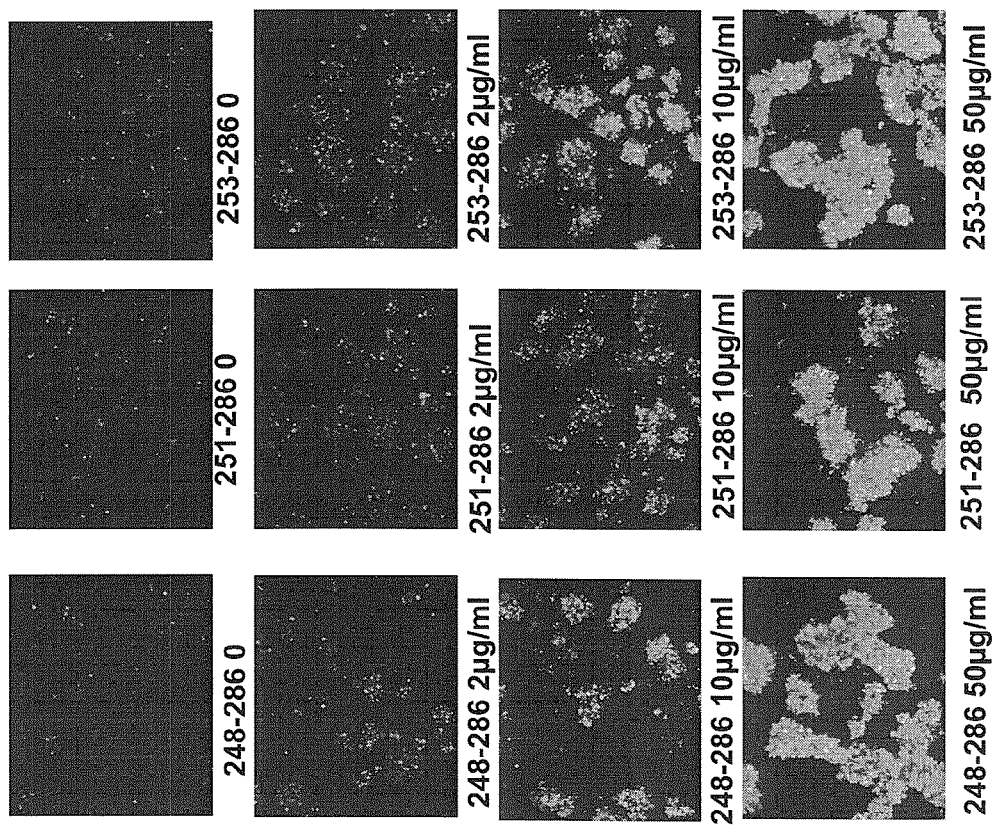

PAP Derived Fragments Enhance the HIV-1 Infection Rate 20,000 CEMX174 5.25 M7 cells encoding LTR-luc and LTR-GFP, sown out in 50 µl RPMI (100% FBS), were incubated with 10 µl of indicated fibrilar peptide dilutions and infected with 0.3 ng p24 antigen of HIV-1 NL4-3 in a total volume of 100 µl. The rate of virus infection was detected after 2 days by performing first UV microscopy (FIG. 10A) and thereafter by measuring luciferase activities of cell lysates of the same samples (FIG. 10B). Fibrilar PAP(248-286), PAP(251-286) and PAP(253-286) dose dependently promoted NL4-3 infection. After infection of control samples containing no peptide, 2.6% of the cells expressed GFP corresponding to luciferase activities of 44,457 RLU/s (FIG. 10). In the presence of 2 µg/ml SEVI the average infection rates were nearly doubled to 4.6% (66,327 RLU/s). At the highest concentration of 50 µg/ml more than 99% of the cells became infected by HIV-1. Median luciferase activities in those samples were 1,701,156 RLU/s, corresponding to a 38 fold increase of infection (1,701,156 RLU/s divided by 44,457 RLU/s of control cells). Our data demonstrate, that PAP derived peptides dramatically enhance the number of HIV-1 infected cells.

Example 10

SEVI Promotes HIV-1 Infection of PBMC and Macrophages Independently of the Coreceptor Usage To productively infect a target cell, HIV-1 requires the primary CD4 receptor and a second molecule on the cell surface, one of the coreceptors CCR5 or CXCR4 (Chantry et al.; 2004). Previous data were obtained with HIV-1 NL4-3 which is strictly CXCR4 (X4) tropic (Papkalla et al.; 2002). To analyze whether SEVI also promotes infection of primary cells with X4 and R5 tropic HIV-1, experiments in peripheral blood mononuclear cells (PBMC) were performed. PBMC were obtained from whole blood using Ficoll density gradient centrifugation (Munch et al.; 2002). Purified PBMC were stimulated for 3 days in RPMI-1640 medium containing 200% FBS, 10 ng/ml IL-2 (Stratmann) and 3 µg/ml phytohemagglutinine (Oxoid; #30852801). Then, PBMC were sedimented by centrifugation at 1200 rpm and resuspended in RPMI1640 (100% FBS, 10 ng/ml IL-2). Next, $5 \times 10^5$ cells were sown out in a volume of 50 µl RPMI and 10 µl of peptide dilutions (fibrilar PAP(248-286)) were added. Subsequently cells were infected with 10, 1 und 0.1 ng p24 antigen of the R5 tropic HIV-1 005-pf-103 (a) (Papkalla et al.; 2002) and the X4 tropic HIV-1 NL4-3 Luc (He at al.; 1995) (b) in a total volume of 100 µl. Both viruses were obtained by transient transfection of 293T cells and contain the luciferase gene instead of nef. Three days post infection cells were pelleted and lysed in 30 µl luciferase lysis buffer. Luciferase activity was detected using 20 µl of lysates and 100 µl of luciferase assay reagent. The increase of luciferase activities with increasing concentrations of peptide demonstrate that SEVI dose dependently promoted infection of PBMC by R5 (FIG. 11A) and X4 (FIG. 11B) tropic viruses. For example, after infection with 1 ng p24 antigen of the R5 tropic HIV-1 or 10 ng of the X4 tropic HIV-1, luciferase activities from samples containing 10 µg/ml SEVI (28,520 RLU/s or 589,840 RLU/s, respectively) were increased 34 or 28 fold compared to reporter activities from control samples containing no peptide (830 RLU/s or 20,820 RLU/s, respectively).

To analyze the effect of SEVI on HIV-1 infection of macrophages, $5 \times 10^5$ PBMC were sown out in 500 µl RPMI (100% FBS, 10 ng/ml GM-CSF) in 48 well dishes (Becton-Dickinson; #353078). After 5 days non adherent cells were carefully washed and 400 µl of fresh medium containing GM-CSF were added. Two days later medium was removed, 130 µl of fresh medium and 20 µl of fibrilar PAP(248-286) dilutions were added to the differentiated macrophages and then infected with the indicated amounts of the X4 tropic NL4-3 Luc (a) and the R5 tropic 005pf103 Luc (b) in a total volume of 200 µl. Virus infection was detected after 3 days using the Luciferase assay reagent. As shown in FIG. 12, SEVI also enhanced HIV-1 infection of macrophages independently of the coreceptor used. Overall infection rates of the X4 tropic NL4-3 (FIG. 12B) are reduced compared to those obtained with the R5 tropic (FIG. 12A) variant because of the lack of CXCR4 expression in macrophages.

Example 11

SEVI Lowers the Threshold of a Productive HIV-1 Infection

To establish productive HIV-1 infection in cell culture, one single infection event must take place. To analyze whether SEVI allows HIV-1 infection of target cells that would not take place under normal conditions without peptide, target cells were incubated with SEVI and infected with virus concentrations that are not sufficient to infect a single cell. 4,000 TZM-bl cells sown out the day before were incubated in 50 µl DMEM, 10 µl fibrilar PAP(251-286) dilutions and infected in a total volume of 100 µl with HIV-1 NL4-3 (X4) and HIV-1 NL4-3 YU-2 (R5) (Papkalla et al., 2002). 0.6 pg and 0.1 pg of p24 antigen correspond to 40 µl of a 15,625 or 78,125 fold diluted viral stock solution. Virus infection was detected after 3 days using the Gal Screen Kit. Average β-galactosidase activities in cells infected with 0.1 and 0.6 pg X4 and R5 tropic HIV variant were similar to that of uninfected cells (n), indicating that no infection took place in samples containing no peptide (FIG. 13A). In contrast, in the presence of 2 µg/ml SEVI or more, infections were readily detectable for all concentrations of virus used. Similar results were obtained when PBMC (for preparation see above) were infected with low amounts of HIV. $5 \times 10^5$ PHA/IL-2 stimulated PBMC were sown out in 96 well dishes (50 µl; 10% FBS, 10 ng/ml IL-2), 10 µl of a 20 µg/ml stock solution of PAP(248-286) were added and subsequently infected with the indicated p24 antigen amounts of NL4-3 in a final volume of 100 µl (final SEVI concentration: 2 µg/ml). One day post infection cells were pelleted to remove peptide and virus and resuspended in 200 µl RPMI (200% FBS, 10 ng/ml IL-2) without SEVI. Supernatants were collected at regular time points and fresh medium was added. Virus replication was assayed using a p24 antigen ELISA. When SEVI containing cells were infected with 120 and 12 pg p24 antigen, HIV-1 replicated with faster kinetics and to higher levels than in control cells without peptide (FIG. 13B). After infection of PBMC with 1.2 and 0.12 pg, virus only replicated in samples containing SEVI but not in control cells without peptide. These data obtained in PBMC and TZM-bl cells clearly demonstrate that SEVI allows the infection of target cells with amounts of HIV-1, that are under the same experimental conditions not infectious at all. To analyze how efficiently SEVI activates HIV infectivity, an endpoint titration of HIV-1 NL4-3 in the presence of different amounts of fibrilar PAP(248-286) using 10 fold dilutions of viral stock solution was performed in CEMX174 5.25 M7 cells. The highest dilution of HIV-1 yielding detectable luciferase activities in control cells containing no peptide was $10^4$ (Table 1). However, in the presence of 0.4 and 2 µg/ml SEVI, HIV-1 infections could also be detected when using log 5 or log 6 dilutions. At the highest SEVI concentration (10 µg/ml) also a log 7 dilution yielded a productive infection. Thus, SEVI dramatically lowers the threshold of HIV-1 infection by 2 to 3 orders of magnitude. The presence of an HIV activating peptide in human sperm could have great implications in the natural transmission of HIV-1 or HIV-2 during sexual intercourse. The HIV-1 transmission rate per sexual contact is lower than 0.1%.

Example 12

Figure 14:
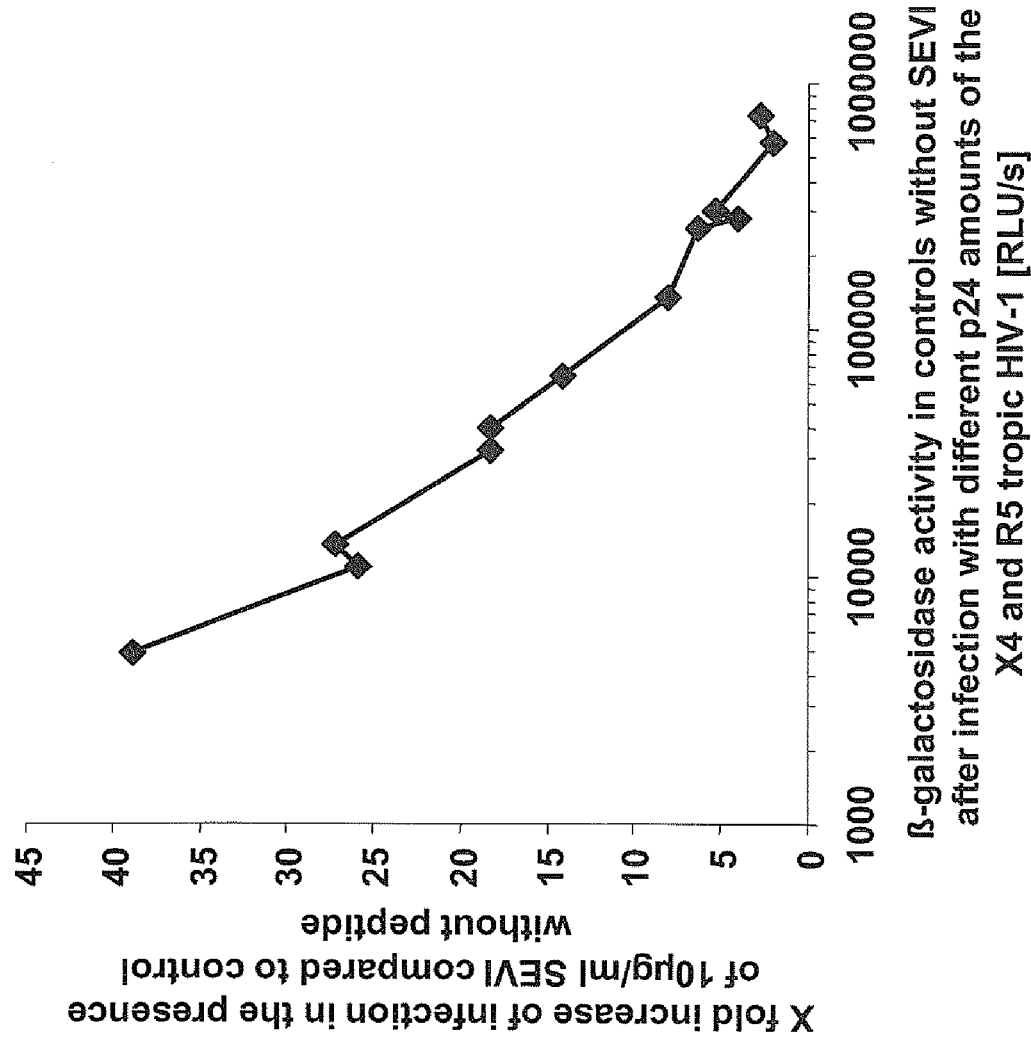

SEVI Mediated Increase of HIV-1 Infection Correlates with Absolute Viral Infectivities Previous experiments have shown that the higher the increase of infection rates in the presence of SEVI were the lower the viral inoculum or MOI (multiplicity of infection) was. To analyze this correlation in more detail, 10 µl of fibrilar PAP(251-286) dilutions were added to 4000 TZM-bl cells (50 µl). Infections were performed with decreasing p24 concentrations of the X4-tropic HIV-1 NL4-3 and the R5 tropic HIV-1 YU2 (Papkalla et al.; 2002) in a total volume of 100 µl. When adding the absolute infectivities/β-galactosidase activities obtained as RLU/s in control samples without peptide for each virus infection dose on the x-axis and the x-fold increase of infection in the presence of 10 µg/ml SEVI for each infection dose on the y-axis, a direct correlation between absolute infectivities and SEVI's activating effect on virus infection could be determined (FIG. 14). The higher the absolute infection rates were, the lower was the effect on SEVI mediated enhancement of infection, and vice versa. This correlation can be partially explained by the fact, that when already a high percentage of cells (i.e. 50%) is infected in control samples, SEVI can only enhance the infection rate to 100%, a maximal increase of the infection rate of factor 2. In contrast when cells are infected with low MOI's (i.e. infection rate 2% in control cells) SEVI can enhance virus infection by several orders of magnitude.

Example 13

Figure 15:
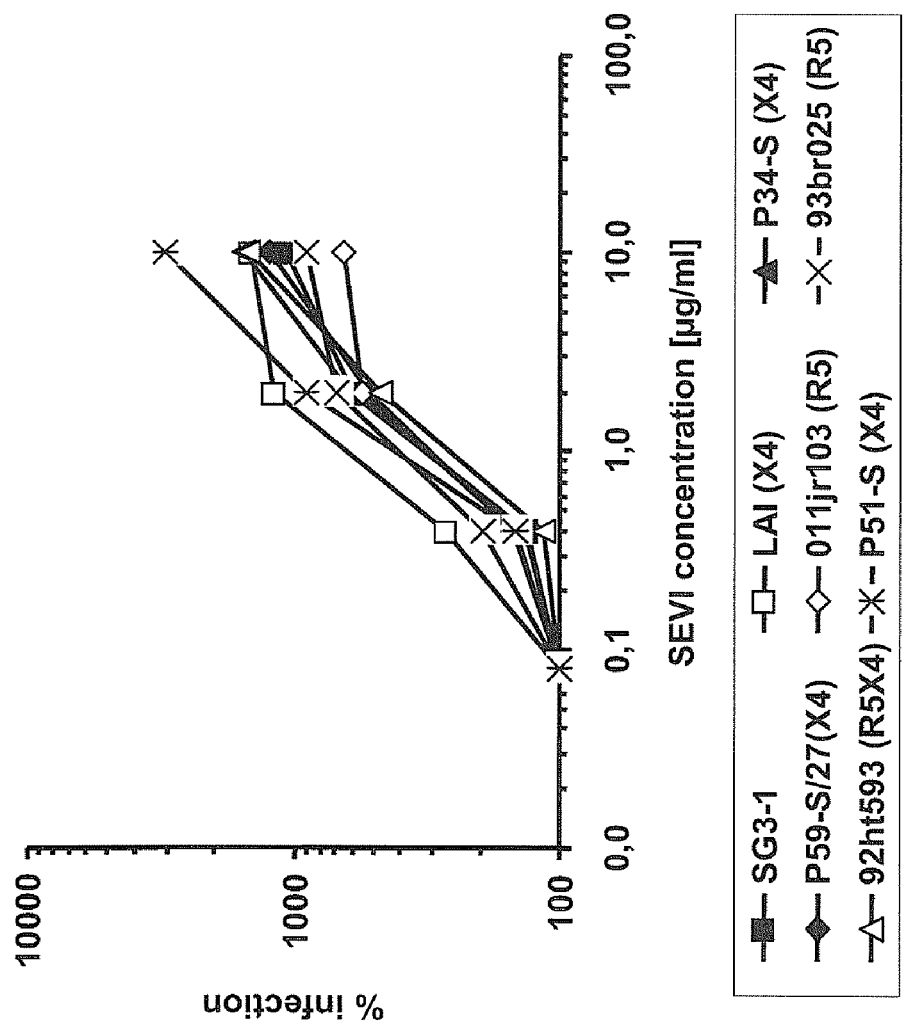

SEVI Promotes the Infection of Several X4, R5 and Dual-Tropic HIV-1 Variants, Molecular HIV Clones and Different HIV-1 Subtypes To detect the enhancing effect on infection by several HIV-1 variants, fibrilar PAP (253-286) dilutions were added in a volume of 10 µl to 50 µl TZM-bl cells sown out the day before. Infections with NL4-3 V3 recombinant viruses (Papkalla et al.; 2002), differing in their coreceptor usage, and molecular HIV-1 clones (obtained through the NIH AIDS Research and Reference Program) were performed using an MOI between ~0.01-0.001 in a total volume of 100 µl. Viral infection was measured using the Gal Screen Kit. SEVI promoted the infection of all tested HIV-1 variants, independently of coreceptor choice or subtype (FIG. 15). In the presence of 0.4 µg/ml SEVI, HIV-1 LAI or 93br025-9 infected cells 2.7 or 1.9 fold more efficiently than control cells without peptide. At higher concentrations SEVI stimulated the infection of all viruses tested more dramatically with a maximum infectivity of 3,045% compared to infected controls without peptide in the case of P51-S. To analyze the effect of SEVI on HIV-1 group 0 isolates (Dittmar et al.; 1999) and various HIV-1 subtypes (NIH AIDS research and reference program), CEMX174 5.25 M7 cells were infected with different MOI's in the presence of different SEVI concentrations. As shown in Table 2, SEVI favoured the infection of all HIV-1 subtypes (A, B, C, D, F) tested with a maximum x-fold increase of luciferase activity compared to control cells of 156 for HIV-1 92UG029. Similar results were obtained when HIV-1 group 0 isolates were tested (Table 3).

Example 14

Mechanism of Action

Figure 16:
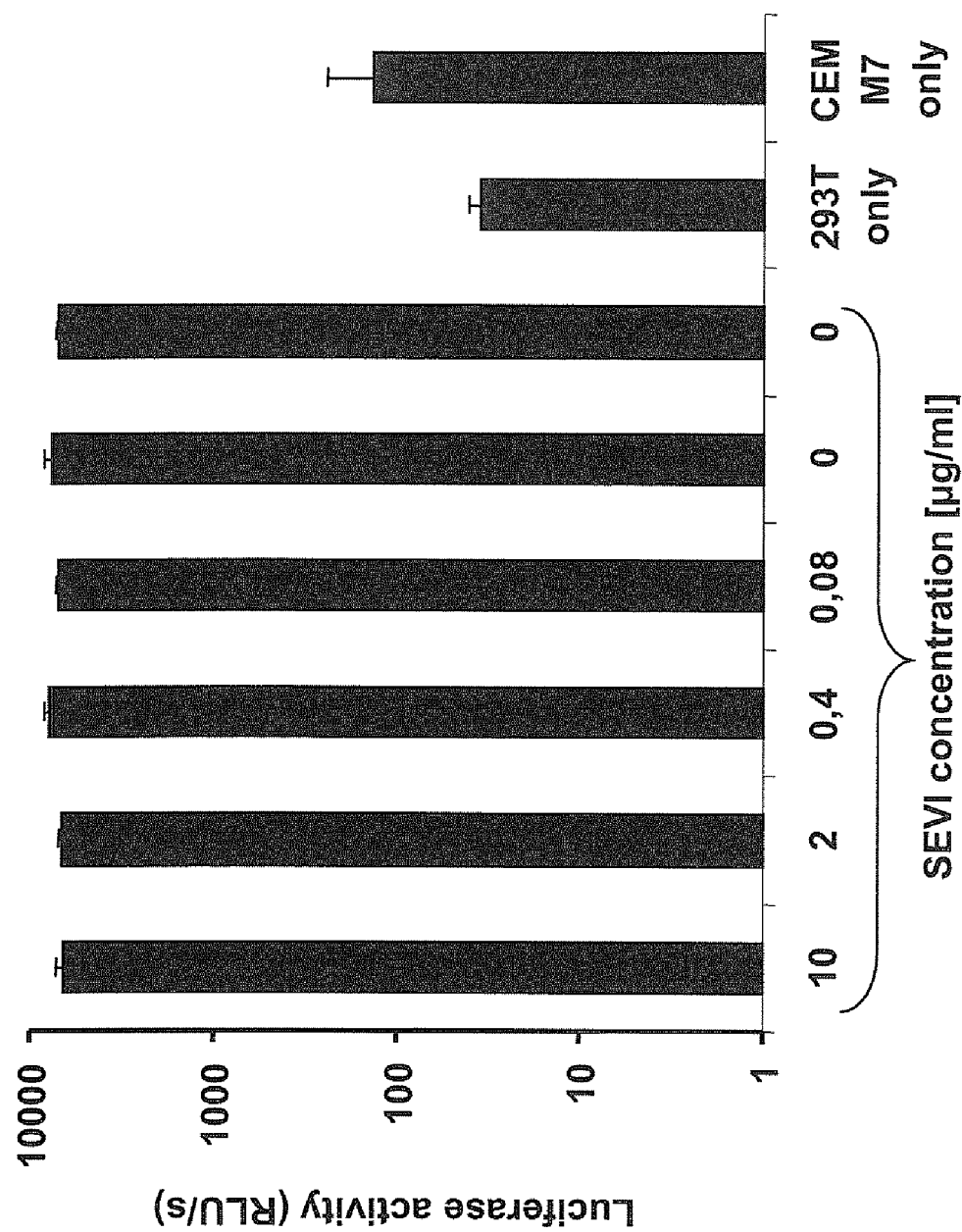

To rule out how SEVI promotes HIV-1 infection, a cell-cell fusion assay based on the HIV-1 env protein was performed (Pöhlmann et al.; 1999). 293T cells, transfected with expression plasmids encoding SIV-Tat and NL4-3 Env, were sown out in 96 well dishes, incubated with different concentrations of fibrilar PAP(248-286) and were cocultivated with CEMX174 5.25 M7 cells in a total volume of 100 µl. The HIV-1 envelope protein, expressed at the cellular membrane of 293T cells, induces the fusion with CD4 and coreceptor positive CEMX174 5.25 M7 cells. When 293T and CEMX174 5.25 M7 cells fused, the 293T expressed viral Tat protein diffuses in the nucleus of the CEMX174 5.25 M7 cells and transactivates the expression of the CEMX174 5.25 M7 cell encoded LTR-luc and LTR-GFP genes. One day later HIV-1 Env mediated fusion rate was detected by measuring luciferase activities in cellular lysates and by performing UV microscopy. Even at a concentration, where SEVI strongly promotes HIV-1 infection, no increase in fusion activity could be observed (compare 10 µg/ml and 0 µg/ml; FIG. 16). UV microscopy revealed that the number of GFP expressing cells were similar in all cocultivated samples. Since only ~2% of the cells were GFP positive, Env was not over expressed.

Example 15

SEVI Interacts with HIV and Promotes Cell Binding

SEVI could bind to viral particles and increase their infectivity, or enhance the susceptibility of target cells to HIV-1 infection. To distinguish between these possibilities, we pre-incubated the virus stock with various concentrations of fibrilar PAP(248-286) for 5 min in a small volume and subsequently added the virus/SEVI mixture to the cell culture, thereby diluting it 50-fold. For comparison, SEVI was directly added to the cell culture and subsequently infected with the same viral dose. The results demonstrated that the efficiency of infectivity enhancement was just dependent on the concentration of SEVI in the presence of virus (FIG. 17A, left). Diluting the HIV-1/SEVI mixture after a brief preincubation period did not at all reduce the magnitude of SEVI-mediated infectivity enhancement. In relation to the final peptide concentration in the infected culture, viral infectivity was enhanced by 50-fold (FIG. 17A, right). These data suggest that SEVI interacts directly with the viral particle and imply that binding is largely complete after 5 min of incubation.

To further assess how SEVI might enhance HIV-1 infection we incubated TZM-bl cells for 3 hs with viral particles in the presence or absence of fibrilar PAP(248-286). Thereafter, unbound virus was removed by extensive washing and the amount of cell-associated p24 antigen was determined by ELISA. SEVI increased binding of HIV-1 to the target cells up to 8-fold in a dose-dependent manner (FIG. 17B, left). Notably, SEVI also enhanced binding of HIV-1 particles lacking Env, although the overall levels of cell-associated p24 were about 30-fold lower than those measured using wildtype HIV-1 particles (FIG. 17B, right). These results suggest that SEVI enhances HIV-1 infection by promoting binding of viral particles to the cell surface.

Example 16

Peptide Fractions Derived from Human Seminal Fluid Promote HIV-1 Infection 2-3 ml of sperm obtained from individual donors was prepared in an analytical scale as described above and the obtained seminal plasma preparation was separated by a single reverse phase chromatographic step prior to the activity determinations. To optimize the chromatographic conditions, the retention time for synthetic SEVI peptides was determined and considered for fractionation and activity determinations in the seminal plasma fractions.

Figure 18:
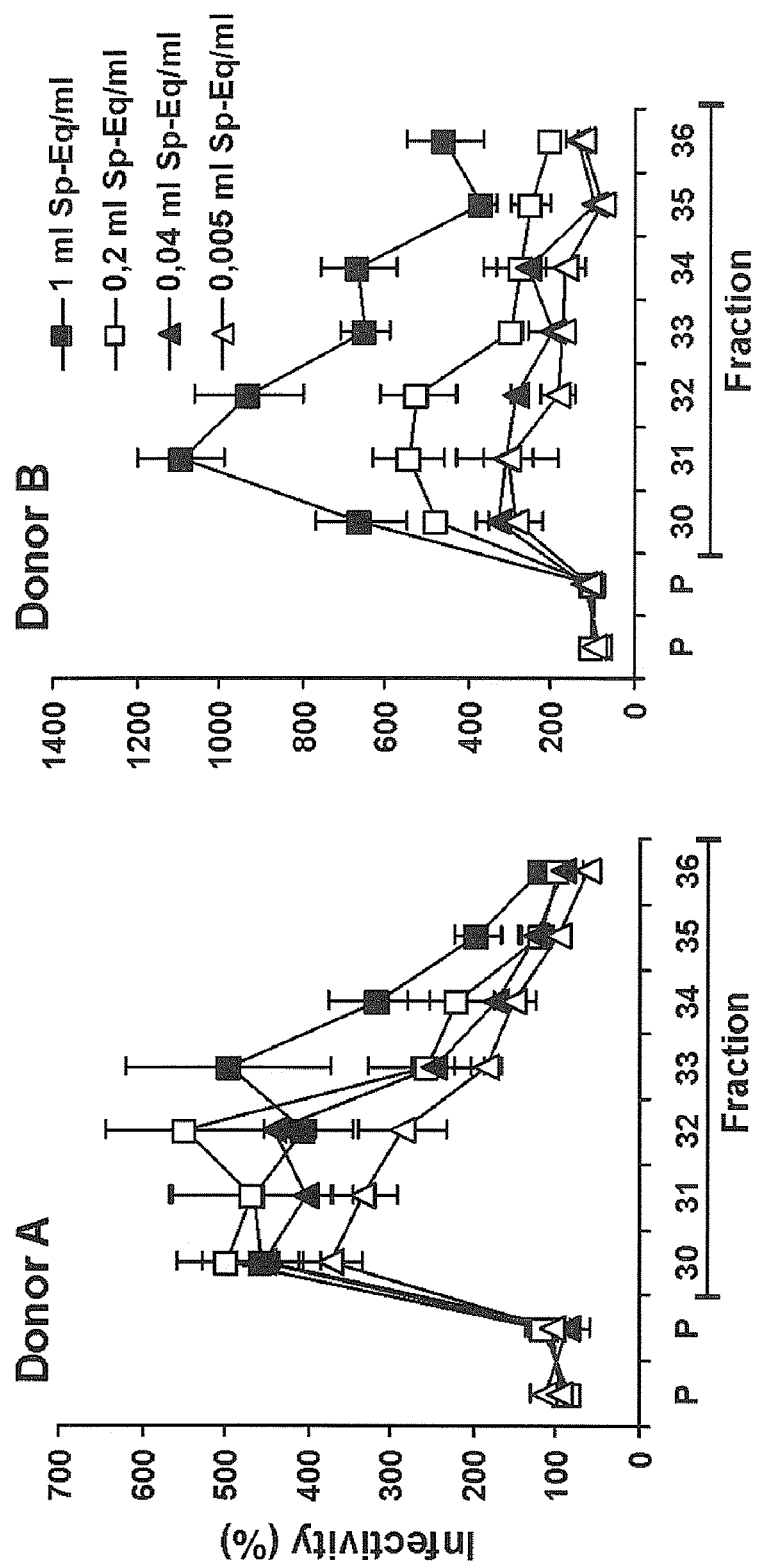

Peptide fractions containing 1 ml sperm equivalent (Sp-Eq) were dissolved in 100 µl DMEM (stock solution 10 ml Sp-Eq/ml). Stock solutions were 5 fold diluted in 96 well U shaped plates in DMEM and 10 µl of dilutions were added to 50 µl TZM-bl cells sown out the day before in 96 well flat bottom plates. Subsequently infections were performed with 0.1 ng p24 antigen of HIV-1 NL4-3 in a total volume of 100 µl. 3 days thereafter infectivity was measured using the Gal Screen kit. At concentrations corresponding to those present in the original seminal fluid (1 ml Sp-Eq/ml), fractions 30-34 from both donors enhanced HIV-1 infection dramatically, e.g. fraction 31 from donor B induced an ~11 fold increase of infectivity compared to control samples (FIG. 18). Strikingly, even a 200-fold dilution of the peptide mixtures derived from some donors efficiently enhanced HIV-1 infection (see Donor A). Taken together, our results strongly suggest that active SEVI fragments are present in human sperm at concentrations well within the range required to promote HIV-1 infection.

Example 17

SEVI Enhances SIV, HIV-2, MuLV and Pseudoparticle Infection of Target Cells

To analyze the effect of SEVI on other retroviruses like lentiviruses, we tested HIV-2 and Simian Immunodeficiency Viruses (SIV). All viral stocks were generated by transient transfection of 293T cells with proviral DNA. The HIV-2ROD10 clone was obtained from K. Strebel (Clavel et al.; 1986), SIVagm-tan 1 from african green monkeys and SIVcpz-tan 1 from chimpanzees were purchased by B. Hahn (Birmingham, Ala., USA). Fibrilar PAP(248-286) dose dependently enhanced infection rates of HIV-2 and different SIV's (FIG. 19). For example, when TZM-bl cells were infected with 2 μl of HIV-2, 50 μg/ml SEVI increased viral infection by two orders of magnitude (FIG. 19A). SEVI also favoured SIVmac and SIVagm infection in TZM-bl (FIG. 19B) and SIVcpz in CEMX174 5.25 M7 cells (FIG. 19C). This data indicate that SEVI enhances infectivities of different primate lentiviruses like HIV-1, HIV-2 and SIV in different cell lines. To analyze whether the stimulating effect of SEVI on lentiviral infection is dependent from the lentiviral Env protein, we replaced the env genes in pBRHIV-1NL4.3 and pBRSIVmac239 by the MuLV env gene resulting in the generation of replication competent HIV-1 (MuLV-HIV) and SIVmac239 (MuLV-SIV) expressing MuLV Env which mediates cell entry (Gundlach et al.; 1998). In the presence of pooled fibrilar PAP fragments, infection rates of MuLV-HIV and MuLV-SIV were dramatically increased (FIG. 20A). Next we analyzed SEVI's effect on infection of MuLV particles carrying the MuLV envelope protein. Therefore an env defect MuLV encoding a luciferase reporter gene (pGC-sam-EN-Luc3; provided by O. Wildner, Bochum, Germany) was pseudotyped with MuLV Env by cotransfection of 293T cells with pGC-sam-EN-Luc3 and pcDNA-MuLV-env resulting in the generation of MLV-MLV particles. In the presence of 2 to 50 μg/ml peptide, MLVpp infected HUH-7 (derived from IPF Pharmaceuticals, Hannover, Germany), PM1 and Jurkat (NIH AIDS research and reagent program) cells in average 10 times more efficiently than control cell containing no SEVI (FIG. 20B). These data demonstrate that SEVI enhances the infectivity/transduction rates of both lentiviruses (HIV, SIV) and oncoviruses (MuLV) that are widely used in gene therapy approaches. Furthermore we could show that SEVI also enhanced infection of env intact or defective HIV-1 particles carrying the G-protein of the Vesicular Stomatitis Virus (FIG. 21A). VSV-G (Cronin et al.; 2005) is widely used to pseudotype retroviral gene therapy vectors because the VSV-G protein allows efficient entry into cells. In addition, SEVI also favoured infection of HIV-1 particles containing the Ebola spike protein (Baribaud et al.; 2002; FIG. 21B).

FIGURES

FIG. 1. Purification of SEVI from seminal fluid. For details see examples 1 and 2. A) Batch fractionation of human seminal plasma by cation exchange chromatography using nine different buffers and pH conditions (pool fractions I-IX). B) The pooled fractions 7-9 from A were subjected to RP-HPLC and the resulting fractions were assayed for anti- or proviral activity. P4-CCR5 cells were infected with HIV-1 NL4-3 in the presence or absence of peptides. Virus infectivity was determined by measuring the β-galactosidase activities in the cellular extracts at 3 days post-infection using the Gal Screen Kit from Tropix. The shaded area of the chromatogram in the inlet specifies the active fraction. C) Fractions 29-31 from pH pool 7 were further purified by RP-HPLC and resulting fractions were tested as described above. HIV-1 promoting fraction 43 was analyzed using sequence and mass spectroscopic analysis. Symbols: n, uninfected cells; +, no peptide added. Average values (±SD) of infectivities derived from triplicate infections are shown relative to those measured in the absence of peptides (100%). D) Mass spectrometric and sequence analysis of fraction 43 from 1C revealed the isolation of the SEVI fragment PAP 248-286.

FIG. 2. Purification of SEVI from seminal fluid. A) The pH pool 7 was subjected to RP-HPLC and the resulting fractions were assayed for anti- or proviral activity. P4-CCR5 cells were infected with HIV-1 NL4-3 in the presence or absence of peptides. Virus infectivity was determined by measuring the β-galactosidase activities in the cellular extracts at 3 days post-infection using the Gal Screen Kit from Tropix. The shaded area of the chromatogram in the inlet specifies the active fraction. B) Fraction 29 from pH pool 7 was further purified by RP-HPLC and resulting fractions were tested as described above. HIV-1 promoting fraction 43 was analyzed using sequence and mass spectroscopic analysis. Symbols: n, uninfected cells; +, no peptide added. Average values (÷SD) of infectivities derived from triplicate infections are shown relative to those measured in the absence of peptides (100%).

FIG. 3. SEVI forms fibrils. a, Effect of activated synthetic SEVI, the clear supernatant, and the redissolved pellet, on HIV-1 infection of CEMX174 5.25 M7 cells. b, Electron micrographs of SEVI after overnight agitation and of the corresponding untreated peptide. c, Enhancement of HIV-1 infection by activated and non-activated SEVI and by a 50% to 950% mixture of both.

FIG. 4. Activated SEVI peptides are stainable with Congo red which is indicative for fibril formation. Upper and lower slide: a solution of activated precipitated SEVI peptides (A), non-activated, soluble SEVI (B) and albumine (C) were transferred to poly-lysine-coated slides and stained by Congo red.

FIG. 5. Activated SEVI peptides show the typical birefringence effect (double refraction) of fibrils using polarized light in light microscopy. The same Congo red-stained slides shown in FIG. 4 were used for microscopy: The solution of activated precipitated SEVI peptides (A), non-activated, soluble SEVI (B) and albumine (C).

FIG. 6. Activated SEVI peptides show remarkably differences in color and intensity using fluorescence microscopy. The same Congo Red-stained slides shown in FIG. 4 were used for microscopy: The solution of activated precipitated SEVI peptides (A), non-activated, soluble SEVI (B) and albumine (C).

FIG. 7. Several synthetic PAP fragments stimulate HIV-1 infection. A) Lyophilized peptides were resuspended in DMEM without FBS and incubated for 20 h at 37° C. at 1,400 rpm using a thermo mixer (Eppendorf). 4,000 CEMX174 5.25 M7 cells were incubated with different concentrations of PAP fragments or control peptides (c1-c3) and infected with 30 μg p24 antigen of HIV-1 NL4-3 in a total volume of 100 μl. After 20 h virus infection was detected using the Luciferase assay reagent (Promega). Average values (±SD) of infectivities derived from triplicate infections are shown relative to those measured in the absence of peptides (100%). B) Shown are the peptide sequences analyzed.

FIG. 8. The stimulating effect of SEVI on HIV-1 infection is cell type independent. 2,000 adherent TZM-bl or P4-CCR5 and 5,000 CEMX174 5.25 M7 suspension cells were sown out in a volume of 50 μl. The day after 10 μl SEVI dilutions were added and cells were infected with 1 ng p24 antigen HIV-1 NL4-3 in a total volume of 100 μl. 2 days post infection viral infectivity in TZM-bl or P4-CCR5 cells was detected using the Gal Screen Kit and in CEMX174 5.25 M7 cells using the luciferase assay test. Average values of infectivity derived from triplicate infections are shown relative to those measured in the absence of peptides (100%).

FIG. 9. SEVI has no effect in cell viability or endogenous LTR activity. A) Cytotoxicity assay: 4,000 TZM-bl cells were sown out in a volume of 100 μl in 96 well flat bottom plates, the day after medium was replaced by 90 μl of fresh medium and SEVI dilutions were added to a final volume of 100 μl. After 3 days 10 μl of a 5 mg/ml MTT solution was added and cells were incubated for 4 h at 37° C. Thereafter formazan crystals were dissolved in 1:1 Ethanol/DMSO and OD was measured at 560/650 nm. Average values±SD of ODs derived from hexaduplicate samples are shown relative to those measured in the absence of peptide (100%). B) Endogenous LTR activity: After 3 days incubation with peptides endogenous LTR activity was measured using the Gal Screen Kit. Shown are median β-galactosidase activities±SD derived from 6 samples. RLU/s: relative light units per second.

FIG. 10. PAP derived peptides dramatically enhance HIV-1 infection of CEMX174 5.25 M7 cells. 20,000 CEMX174 5.25 M7 cells encoding LTR-luc and LTR-GFP, sown out in 50 μl RPMI (100% FBS), were incubated with 10 μl of peptide dilutions and infected with 0.3 ng p24 antigen of HIV-1 NL4-3 in a total volume of 100 μl. The rate of virus infection was detected after 2 days by performing UV microscopy (A) or by measuring luciferase activity of cellular lysates (B). RLU/s: relative light units per second.

FIG. 11. SEVI enhances HIV-1 infection in PBMC independently of coreceptor tropism. $5 \times 10^5$ PHA/IL-2 stimulated peripheral blood mononuclear cells (PBMC) were sown out in 50 μl RPMI (100% FBS, 10 ng/ml IL-2). 10 μl of peptide dilutions were added and cells were infected with 10, 1 and 0.1 ng p24 antigen of the R5 tropic HIV-1 005-pf-103 (A) (Papkalla et al., 2002) and the X4 tropic HIV-1 NL4-3 Luc (B) in a total volume of 100 μl. Three days post infection cells were pelleted and lysed in 30 μl luciferase lysis buffer. Luciferase activity was detected using 20 μl of lysates and 100 μl of luciferase assay reagent (Promega). RLU/s: relative light units per second.

FIG. 12. SEVI promotes HIV-1 infection of macrophages. $5 \times 10^5$ PBMC were sown out in 500 μl RPMI (100% FBS, 10 ng/ml GM-CSF) in 48 well dishes. After 5 days non adherent cells were carefully washed out and 400 μl of fresh medium containing GM-CSF was added. Two days later medium was removed, 130 μl of fresh medium and 20 μl of peptide dilutions were added to the cells and then infected with the indicated amounts of the X4 tropic NL4-3 Luc (A) and the R5 tropic 005pf103 Luc (B) in a total volume of 200 μl. Virus infection was detected after 3 days using the Luciferase assay reagent. Data were obtained from a triplicate experiment and represent mean values+/−SD. RLU/s: relative light units per second.

Figure 13:
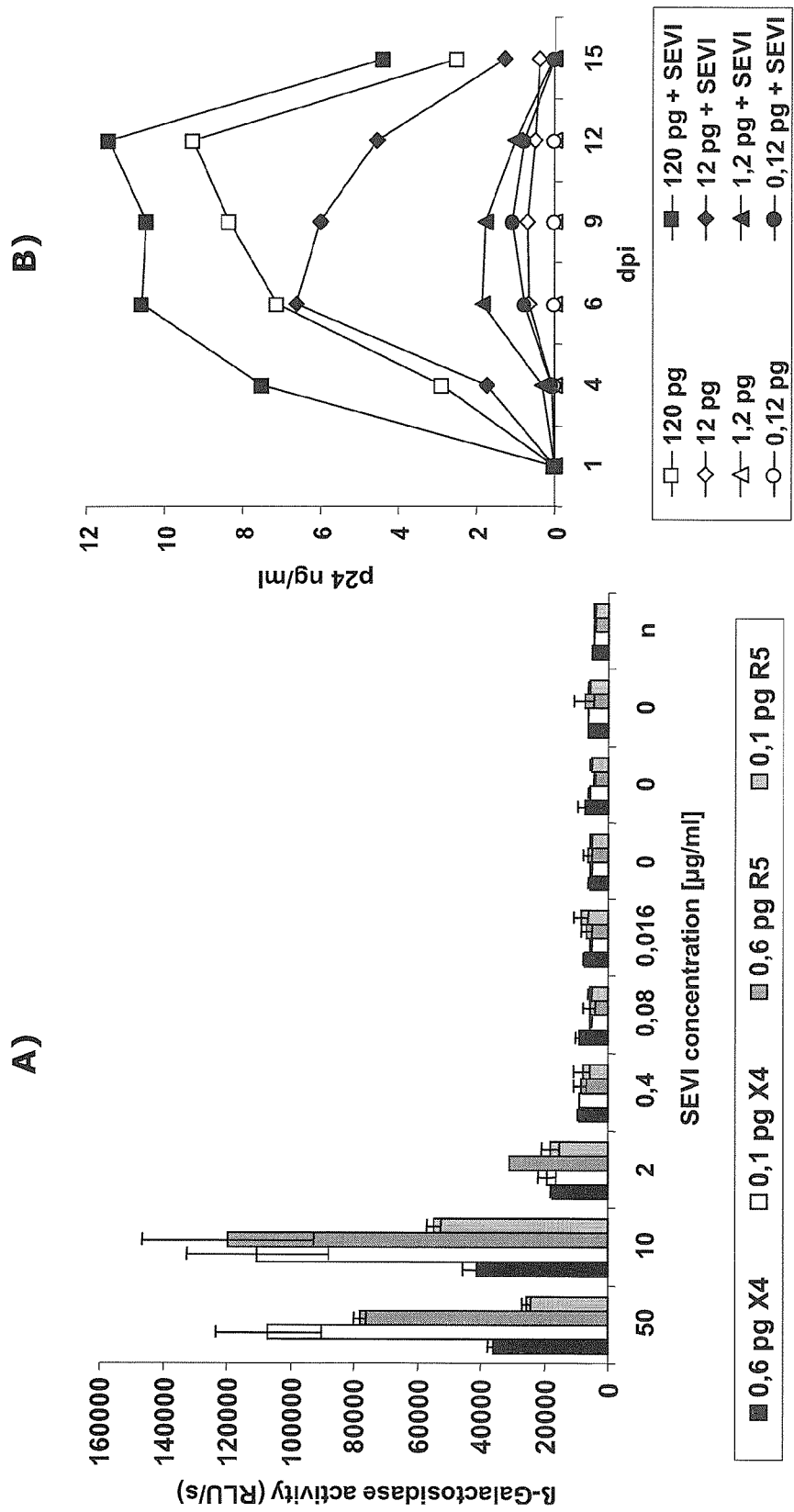

FIG. 13. SEVI lowers the threshold of a productive HIV-1 infection. A) 4,000 TZM-bl cells sown out the day before, were incubated in 50 μl DMEM, 10 μl peptide dilutions and infected in a total volume of 100 μl with HIV-1 NL4-3 (X4) and HIV-1 NL4-3 YU-2 (R5) (Papkalla et al., 2002). 0.6 pg and 0.1 pg of p24 antigen correspond to 40 μl of a 15625 or 78125 fold diluted viral stock solution. Virus infection was detected after 3 days using the Gal Screen Kit. Shown are median values derived from triplicate infections+/−SD; n: uninfected cells; RLU/s: relative light units per second. B) $5 \times 10^5$ PHA/IL-2 stimulated PBMC were sown out in 96 well dishes (50 μl; 10% FBS; 10 ng/ml IL-2), 10 μl of a 20 μg/ml stock solution were added and subsequently infected with the indicated p24 antigen amounts of NL4-3 in a final volume of 100 μl (SEVI concentration 2 μg/ml). One day post infection cells were pelleted to remove peptide and virus and resuspended in 200 μl RPMI (200% FBS; 10 ng/ml IL-2) without SEVI. Supernatants were collected at regular time points and fresh medium was added. Virus replication was assayed using a p24 antigen ELISA (NIH AIDS program). Values represent medians of duplicate infections.

FIG. 14: SEVI mediated increase of HIV-1 infection correlates with absolute viral infectivities. 10 μl SEVI dilutions were added to 4,000 TZM-bl cells (50 μl). Infections were performed with decreasing p24 concentrations of the X4-tropic HIV-1 NL4-3 and the R5 tropic HIV-1 YU2 in a total volume of 100 μl. 2 days post infection viral infectivity was measured using the Gal Screen Kit. Shown are the median absolute β-galactosidase activities (RLU/s) derived from triplicate infections of each virus dilution without peptide α-axis) and the x-fold increase of viral infectivity in the presence of 10 μg/ml SEVI compared to the respective control infection without peptide (y-axis).

FIG. 15. SEVI enhances the infection of X4, R5 and dual tropic HIV-1 variants and several molecular HIV-1 clones. Peptide dilutions were added in a volume of 10 μl to 50 μl TZM-bl cells sown out the day before. Infections with NL4-3 V3 recombinant viruses (Papkalla et al.; 2002) and molecular HIV-1 clones were performed using an MOI between ~0.01-0.001 in a total volume of 100 μl. Virus infection was measured using the Gal Screen Kit. Average values of infectivity derived from triplicate infections are shown relative to those measured in the absence of peptides (100%).

FIG. 16. SEVI has no effect on HIV-1 Env mediated cell-cell fusion. 293T cells, transfected with expression plasmids encoding SIV-Tat and NL4-3 Env, were sown out in 96 well dishes, incubated with different concentrations of SEVI and cocultivated with CEMX174 5.25 M7 cells in a total volume of 100 μl. One day later HIV-1 env mediated fusion rate was detected by measuring luciferase activities in cellular lysates. Shown are median values derived from triplicate infections+/−SD. RLU/s: relative light units per second.

Figure 17:
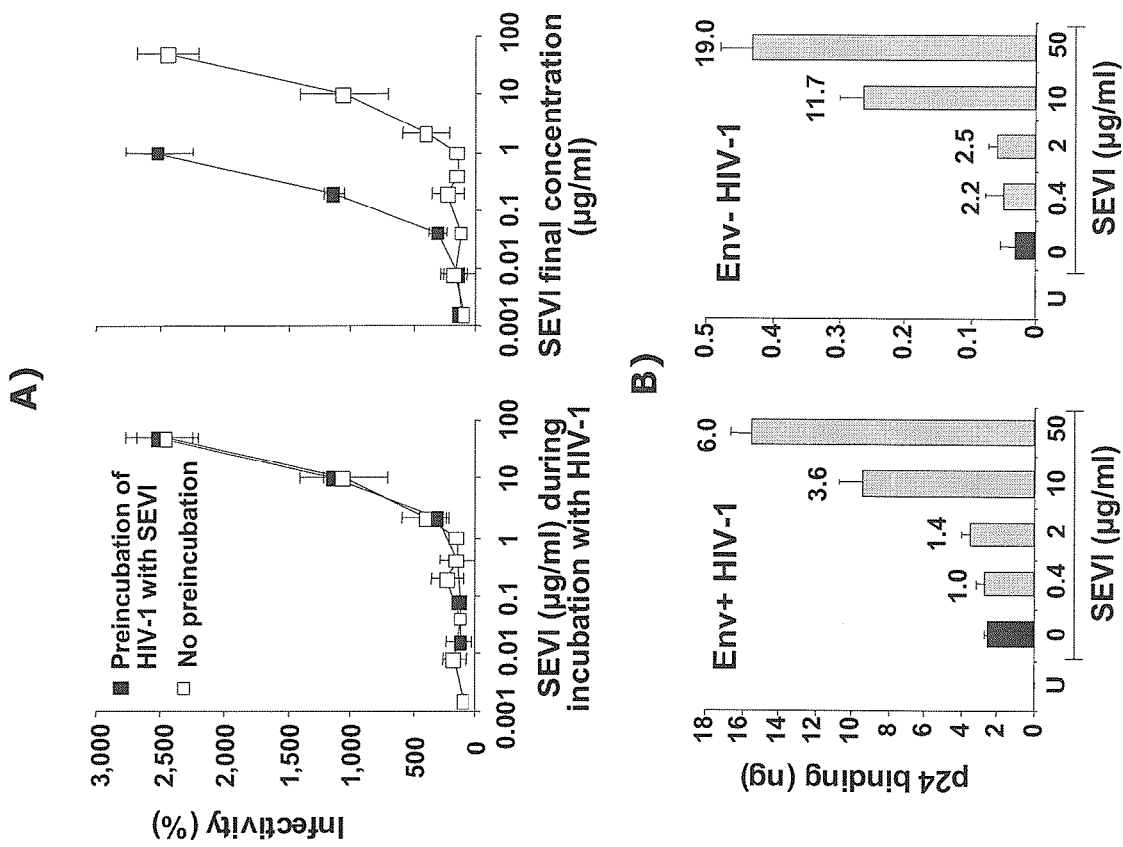

FIG. 17. SEVI interacts with the HIV-1 particle and enhances its binding to the cell. A) Interaction of SEVI with HIV-1. SEVI was either preincubated with the virus stock in a small volume and subsequently added to the cells (□) or SEVI and the HIV-1 stocks were added separately to the cells (■). The SEVI concentrations during incubation with the virus stocks are shown in the left panel and the concentrations relating to the total cell culture in the right panels. B) SEVI enhances binding of wildtype and Env-defective viral particles to the cells. u, uninfected cells. Data represent average values±s.d. (n=3).

FIG. 18. SEVI-containing peptide fractions promote HIV-1 infection. A peptide/protein mixture derived from seminal fluid was separated by a single reversed phase chromatography. Infection of TZM-bl cells with HIV-1 NL4-3 was performed at peptide concentrations corresponding to those present in the original seminal fluid (1 ml Sperm-Equivalent/ml) and 5-fold dilutions thereof. Shown are average values (±SD) obtained from triple infections in the presence of peptide/protein fractions derived from two representative sperm donors 2 days post infection compared to infections without peptide (100%). Absolute infectivities of NL4-3 infection in control samples were ~70,000 RLU/s.

Figure 19:
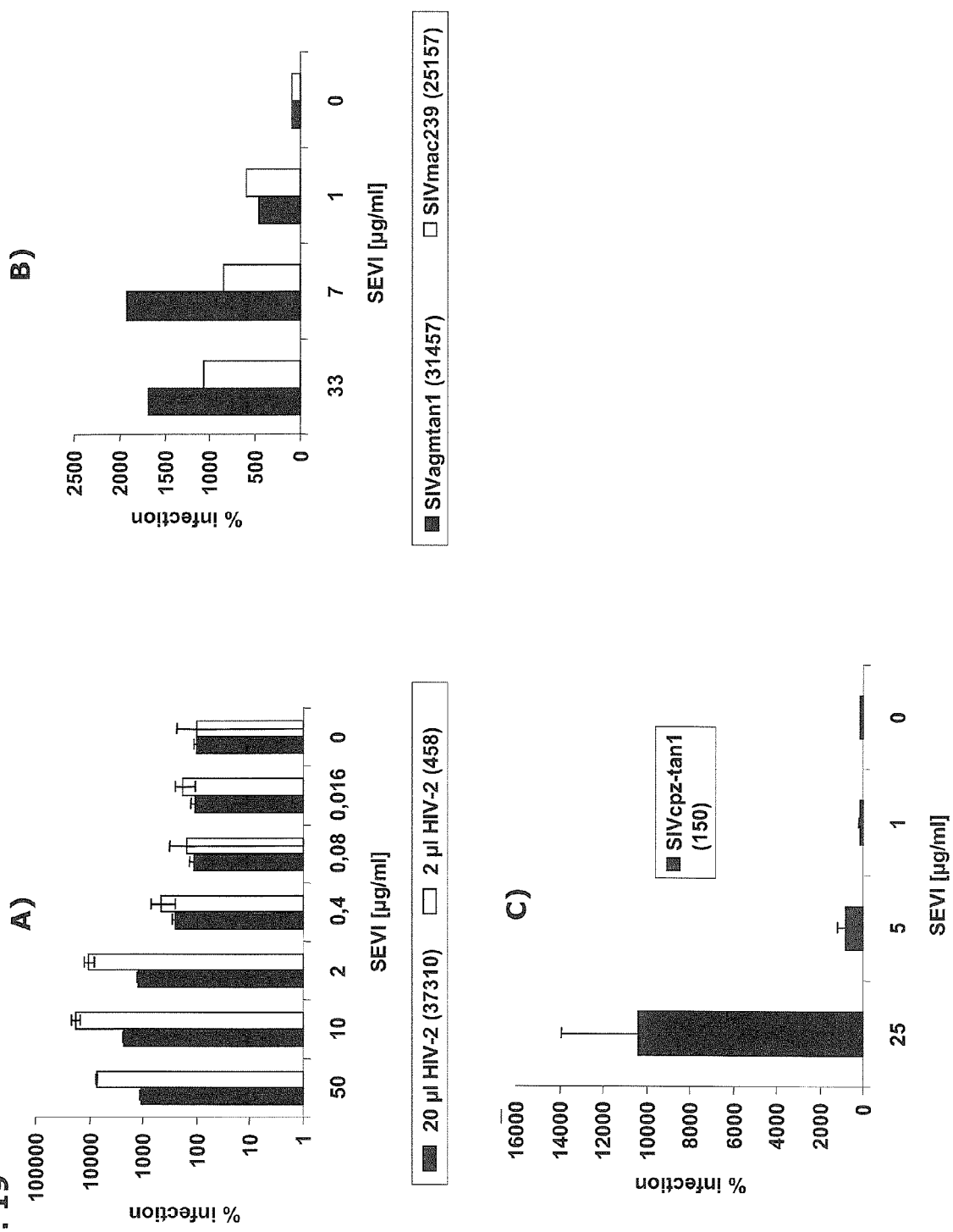

FIG. 19. SEVI favours infection of HIV-2 and SIV's. TZM-bl cells were infected in the presence of indicated amounts of SEVI with 20 and 2 μl of HIV-2 ROD10 (A) or 20 μl of SIVagmtan 1 or SIVmac239 (B). 2 days thereafter infectivities were determined using the Gal Screen assay. The effect of SEVI on SIVcpztan 1 infectivity was determined in CEMX174 5.25 M7 two days post infection (C). Values in brackets give the median absolute infection rates in control samples containing no peptide (0) in RLU/s derived from a triplicate experiment. Numbers in parenthesis give the absolute reporter enzyme activities in RLU/s in control samples without peptide.

Figure 20:
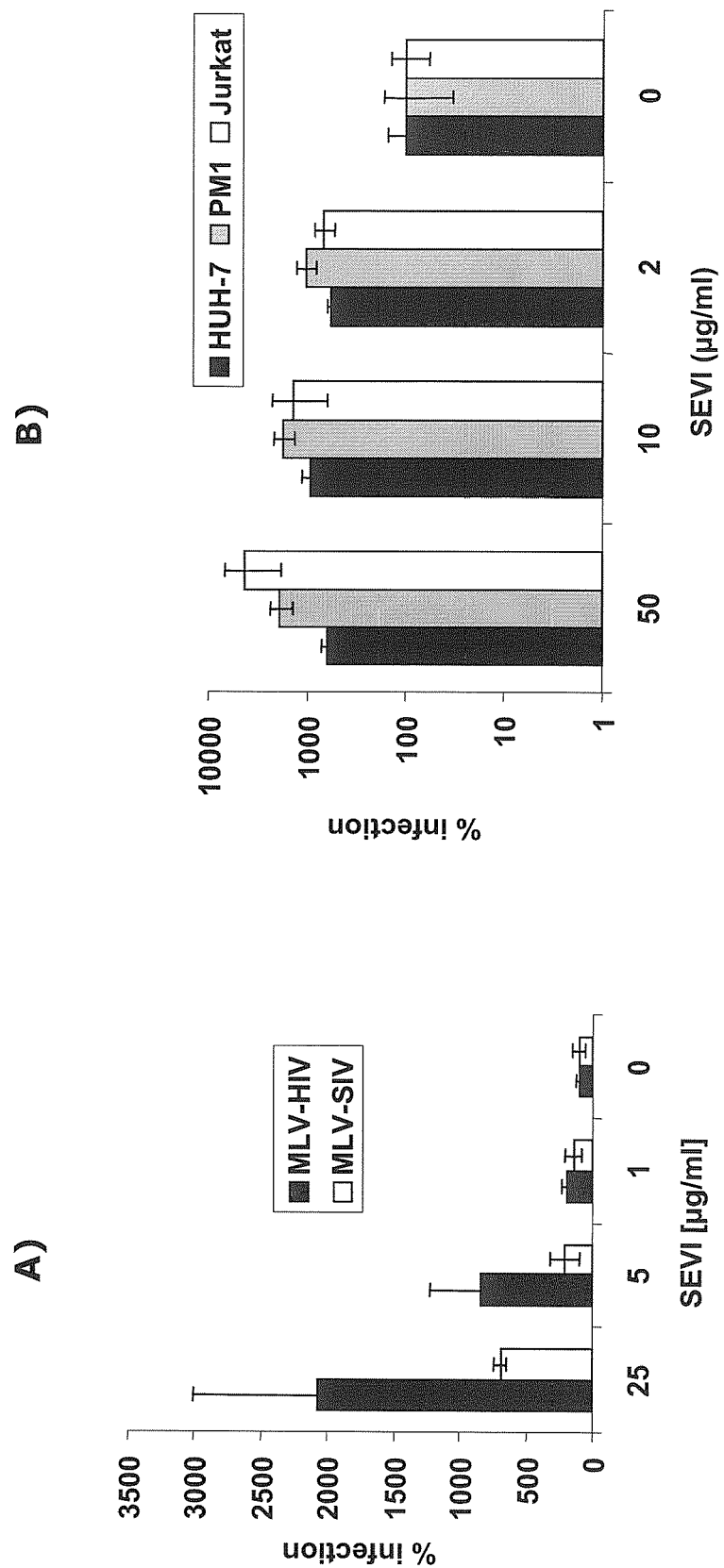

FIG. 20. SEVI favours infection of Mouse Leukemia Virus. A) Effect of SEVI on replication competent HIV (MuLV-HIV) or SIV (MuLV-SIV) expressing MuLV env. 10 µl SEVI solution was added to 50 µl CEMX174 5.25 M7 cells and subsequently infected with 40 µl of 293T transfection derived virus stocks. Infectivities were determined 2 days post infection using the luciferase assay kit. B) Effect of SEVI on MuLV particles pseudotyped with MuLV Env. Viral stocks were generated by cotransfection of 293T cells with an env defective, luciferase expressing proviral MLV DNA (pGC-sam-EN-Luc3; provided by Oliver Wildner, Bochum) and an MLV env expression plasmid. Target cells (HUH7, Jurkat, PM1) were sown out in a volume of 50 µl and 10 µl of peptide was added. Subsequently cells were infected with 40 µl of undiluted or 1:10 diluted virus stock. Luciferase activity in cellular lysates was detected 2 and 3 days post infection. Shown are the median values obtained for each cell line from two independent experiments+/−SD.

Figure 21:
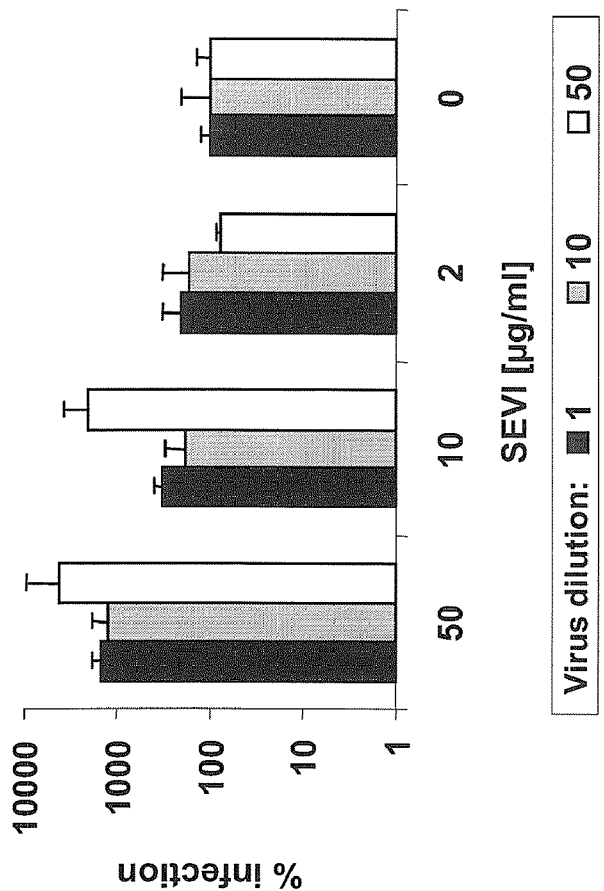
Figure 21:
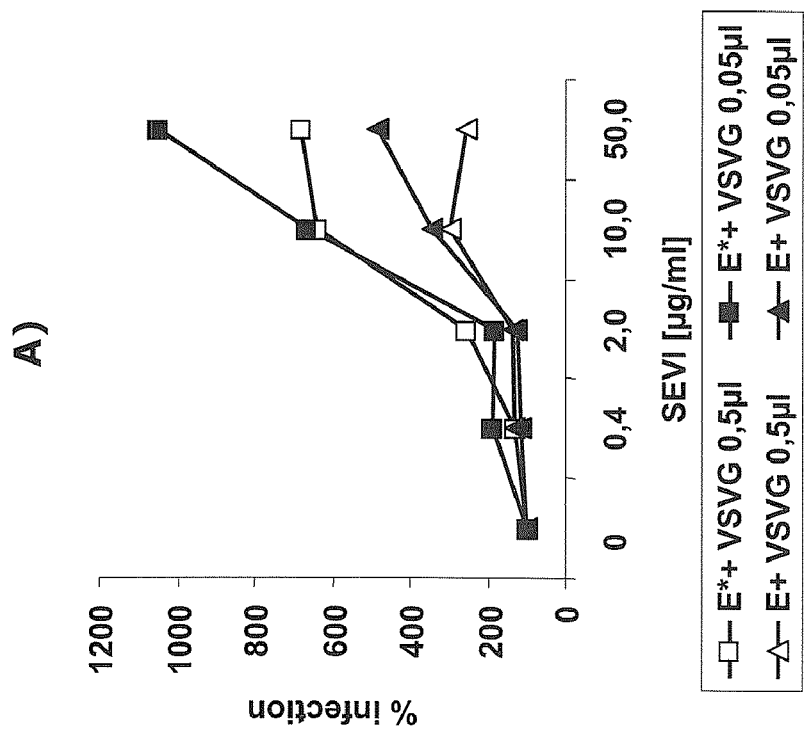

FIG. 21: SEVI enhances infection of VSV-G and Ebola glycoprotein harboring HIV. For pseudotype production 293T cells were cotransfected with equal amounts of the Ebola glycoprotein encoding expression plasmid EBOV-GP or pHIT-VSV-G encoding the G protein of VSV together with env intact (E+) or env defective (E*) luciferase expressing HIV-1 proviral DNA pBRNL4-3-Luc. Cell culture supernatants were harvested 48 h after transfection, passed through 0.4-µm-pore-size filters, aliquoted, and stored at −80° C. A) TZM-bl cells were infected with 0.5 or 0.05 µl of VSV-G pseudotyped E+ or E* HIV-Luc in the presence of indicated amounts of fibrilar PAP(248-286). Infection rates were determined 2 days post infection using the Gal Screen Kit. B) Effect of SEVI on Ebola gp pseudotyped particles. 293T cells were seeded onto 96-well plates at a density of $3 \times 10^4$ per well and incubated o/n at 37° C. Prior to infection medium was completely removed from the cells and replaced by 50 µl medium containing double concentrated peptide (fibrilar PAP (248-286). Infection was performed with 50 µl of serial dilutions (1:undiluted; 10:10 fold dilution; 50:50 fold dilution) of Ebola pseudotyped virus immediately after peptide addition. 12 h after infection medium was replaced and luciferase activity was determined 72 h after transduction with a commercially available kit as recommended by the manufacturer (Promega, Wis., USA).

TABLE 1

Endpoint Titration of HIV-1 in the Presence of SEVI

CEMX174 5.25 M7 cells were sown out in 96 well plates in a volume of 50 pa, 10 µl of SEVI were added and subsequently infected with 40 µl of 10 fold dilutions of HIV-1 NL4-3. Productive infection was measured 3, 5 and 7 dpi using the luciferase assay kit. Cells were considered to be productively infected (p) when absolute luciferase activities were >100 times higher than those obtained from uninfected cells. Numbers in brackets indicate the number of productively infected wells from a triplicate experiment at 7 days post infection.

TABLE 2

SEVI Favours Infection of Different HIV-1 M Subtypes

50 µl CEMX174 5.25 M7 cells were incubated with 10 µl SEVI dilutions and subsequently infected with low MOI's of pretested HIV-1 group M isolates derived from filtrated supernatants of infected CEMX174 5.25 M7 cells. At 1, 2 or 3 days post infection (see column 7) the rate of infection was determined using the Luciferase assay kit. Shown are % infectivities in the presence of 25 and 5 µg/ml SEVI, respectively, compared to control infections containing no peptide (100%). The absolute luciferase activities in RLU/s in control samples are shown in column 4. To calculate the x fold increase of infection in the presence of 25 µg/ml SEVI, absolute RLU/s values obtained in the presence of peptide were divided through luciferase activities from infected control cells containing no peptide. Data were derived from duplicate infections. Each row represents an independent experiment with independently derived virus stocks. R5: CCR5 tropic, X4: CXCR4 tropic variant.

TABLE 3

SEVI Favours Infection of HIV-1 O Isolates

50 µl CEMX174 5.25 M7 cells were incubated with 10 µl SEVI dilutions and subsequently infected with low MOI's of pretested HIV-1 group 0 isolates derived from filtrated supernatants of infected PM1 cells (1639-13470) or CEMX174 5.25 M7 cells (Ca9, MVP5180). At 1, 2 or 3 days post infection (see column 6) the rate of infection was determined using the Luciferase assay kit. Shown are % infectivities in the presence of 25 and 5 µg/ml SEVI, respectively, compared to control infections containing no peptide (100%). The absolute luciferase activities in RLU/s in control samples are shown in column 4. To calculate the x fold increase of infection in the presence of 25 µg/ml SEVI, absolute RLU/s values obtained in the presence of peptide were divided through luciferase activities obtained from infected control cells containing no peptide. Data were derived from single infections. Each row represents an independent experiment with independently derived virus stocks. R5:CCR5 tropic, X4:CXCR4 tropic variant.

TABLE 1

| SEVI concentration | virion # | | | | | | | |
|---|---|---|---|---|---|---|---|---|
| | $5 \times 10^6$ log 1 | $5 \times 10^5$ log 2 | $5 \times 10^4$ log 3 | $5 \times 10^3$ log 4 | $5 \times 10^2$ log 5 | $5 \times 10^1$ log 6 | $5 \times 10^0$ log 7 | $5 \times 10^{-1}$ log 8 |
| 10 | p (3) | p (3) | p (3) | p (3) | p (3) | p (2) | p (1) | n |
| 2 | p (3) | p (3) | p (3) | p (3) | p (3) | p (2) | n | n |
| 0.4 | p (3) | p (3) | p (3) | p (2) | p (2) | n | n | n |
| 0 | p (3) | p (3) | p (3) | N | n | n | n | n |

CEMX174 5.25 M7 cells were sown out in 96 well plates in a volume of 50 µl, 10 µl SEVI were added and subsequently infected with 40 µl of 10 fold dilutions of HIV-1 NL4-3. Productive infection was measured 3, 5 and 7 dpi using the luciferase assay kit. Cells were considered to be productively infected (p) when absolute luciferase activities were >100 times higher than those obtained from uninfected cells. Numbers in brackets indicate the number of productively infected wells from a triplicate experiment at 7 days post infection. The amount of virions (virion #) used for infection was calculated based on the p24 content (ng/ml) of the virus stocks assuming 5000 p24 CA proteins per virion (Briggs et al., 2004).

| Virus | Subtype (gag) | % infection (25 µg/ml) SEVI | % infection (5 µg/ml) SEVI | RLU/s control | x fold increase (25 µg/ml SEVI) | assay (dpi) |
|---|---|---|---|---|---|---|
| 92UG021 (X4) | A | 12924 | 766 | 435 | 129 | 1 |
| 92UG021 (X4) | A | 4165 | 3943 | 8890 | 42 | 2 |
| 92UG029 (X4) | A | 2230 | 223 | 25813 | 22 | 2 |
| 92UG029 (X4) | A | 2145 | 92 | 5418 | 21 | 2 |
| 92UG029 (X4) | A | 15640 | 4468 | 4705 | 156 | 2 |
| 92US723 (X4R5) | B | 2493 | 128 | 5730 | 25 | 2 |
| 92US723 (X4R5) | B | 2670 | 191 | 708 | 27 | 2 |
| 97ZA009 (R5) | C | 9233 | 306 | 3148 | 92 | 2 |
| 97ZA009 (R5) | C | 2801 | 91 | 573 | 28 | 2 |
| 98IN022 (R5) | C | 1331 | 188 | 35435 | 13 | 2 |
| 98IN022 (R5) | C | 2614 | 203 | 2315 | 26 | 2 |
| 92UG024 (X4) | D | 1180 | 141 | 8028 | 12 | 1 |
| 92UG024 (X4) | D | 1248 | 205 | 46323 | 12 | 2 |
| 92UG005 (R5) | D | 980 | 88 | 2930 | 10 | 2 |
| 92UG005 (R5) | D | 1128 | 404 | 3950 | 11 | 3 |
| 93BR020 (X4R5) | F | 1369 | 143 | 1453 | 14 | 2 |
| ARP173/RU570 (R5) | G | 7029 | 3238 | 240 | 70 | 1 |
| ARP173/RU570 (R5) | G | 4874 | 4324 | 8415 | 49 | 2 |
| jc (X4) | ? | 1260 | 155 | 29885 | 13 | 2 |
| jc (X4) | ? | 1867 | 113 | 2155 | 19 | 2 |

| Virus | % infection (25 µg/ml) SEVI | % infection (5 µg/ml) SEVI | RLU/s control | x fold increase (25 µg/ml SEVI) | assay (dpi) |
|---|---|---|---|---|---|
| 1639 (R5) | 9878 | 1548 | 115 | 99 | 2 |
| 1639 (R5) | 19700 | 2200 | 60 | 197 | 3 |
| 2171 (X4) | 30753 | 13068 | 295 | 308 | 2 |
| 2901 (R5) | 12214 | 1039 | 355 | 122 | 1 |
| 2901 (R5) | 4811 | 2758 | 6535 | 48 | 2 |
| 8161 (X4) | 2212 | 1969 | 1660 | 22 | 1 |
| 8162 (X4) | 1211 | 895 | 29380 | 12 | 2 |
| 8913 (R5) | 3977 | 3081 | 1035 | 40 | 1 |
| 8913 (R5) | 3630 | 3284 | 10460 | 36 | 2 |
| 9435 (R5) | 30367 | 8024 | 705 | 304 | 2 |
| 9435 (R5) | 5194 | 1924 | 475 | 52 | 2 |
| 13127 (R5) | 3171 | 1862 | 2650 | 32 | 1 |
| 13127 (R5) | 3699 | 2453 | 15400 | 37 | 2 |
| 13470 (R5) | 10699 | 600 | 365 | 107 | 1 |
| 13470 (R5) | 3744 | 868 | 8965 | 37 | 2 |
| Ca9 | 9285 | 280 | 2903 | 93 | 2 |
| Ca9 | 1398 | 53 | 2608 | 14 | 3 |
| mvp5180 (X4R5) | 6417 | 210 | 368 | 64 | 2 |
| mvp5180 (X4R5) | 1471 | 59 | 4563 | 15 | 3 |
| uninfected | 1 | 1 | 80 | 0 | 1, 2, 3 |

REFERENCES

Adachi A, Gendelman H E, Koenig S, Folks T, Willey R, Rabson A, Martin M A. Production of acquired immunodeficiency syndrome-associated retrovirus in human and nonhuman cells transfected with an infectious molecular clone. J Virol. 1986 August; 59(2):284-91.

Apostol I, Kuciel R, Wasylewska E, Ostrowski W S. Phosphotyrosine as a substrate of acid and alkaline phosphatases. Acta Biochim Pol. 1985; 32(3): 187-97.

Aumuller G, Seitz J. Cytochemistry and biochemistry of acid phosphatases. VI: Immunoelectron microscopic studies on human prostatic and leukocytic acid phosphatases. Prostate. 1985; 7(2):161-9

Baribaud F, Pöhlmann S, Leslie G, Mortari F, Doms R W. Quantitative expression and virus transmission analysis of DC-SIGN on monocyte-derived dendritic cells. J Virol. 2002 September; 76(18):9135-42.

Briggs, J., A., Simon, M. N., Gross, I., Krausslich, H. G., Fuller, S. D., Vogt, V. M., and Johnson, M. C. (2004). The stoichiometry of Gag protein in HIV-1. Nat. Struct. Mol. Biol. 11, 672-675.

Chantry D. HIV entry and fusion inhibitors. Expert Opin Emerg Drugs. 2004 May; 9(1):1-7. Review.

Charneau P, Borman A M, Quillent C, Guetard D, Chamaret S, Cohen J, Remy G, Montagnier L, Clavel F. Isolation and envelope sequence of a highly divergent HIV-1 isolate: definition of a new HIV-1 group. Virology. 1994 Nov. 15; 205(1):247-53.

Choe B K, Pontes E J, Rose N R, Henderson M D. Expression of human prostatic acid phosphatase in a pancreatic islet cell carcinoma. Invest Urol. 1978 January; 15(4):312-8.

Choe B K, Pontes E J, Dong M K, Rose N R. Double-antibody immunoenzyme assay for human prostatic acid phosphatase. Clin Chem. 1980 December; 26(13): 1854-9.

Clavel, F., Guyader, M., Guetard, D., Salle, M., Gluckman, J.-C. and Alizon, M. Molecular cloning and polymorphism of the human immunodeficiency virus type 2. Nature 324, 691-695 (1986)

Coffey D S, Pienta K J. New concepts in studying the control of normal and cancer growth of the prostate. Prog Clin Biol Res. 1987; 239:1-73. Review.

Cronin J, Zhang X Y, Reiser J. Altering the tropism of lentiviral vectors through pseudotyping. Curr Gene Ther. 2005 August; 5(4):387-98. Review. Erratum in: Curr Gene Ther. 2005 October; 5(5):531.

Cusan L, Gomez J L, Dupont A, Diamond P, Lemay M, Moore S, Labrie F. Metastatic prostate cancer pulmonary nodules: beneficial effects of combination therapy and subsequent withdrawal of flutamide. Prostate. 1994 May; 24(5):257-61

Derechin M, Ostrowski W, Galka M, Barnard E A. Acid phosphomonesterase of human prostate. Molecular weight, dissociation and chemical composition. Biochim Biophys Acta. 1971 October; 250(1):143-54.

Dittmar M T, Zekeng L, Kaptue L, Eberle J, Krausslich H G, Gurtler L. Coreceptor requirements of primary HIV type 1 group 0 isolates from Cameroon. AIDS Res Hum Retroviruses. 1999 May 20; 15(8):707-12.

Drenckhahn D, Waheed A, Van Etten R. Demonstration of prostatic-type acid phosphatase in non-lysosomal granules in the crypt epithelium of the human duodenum. Histochemistry. 1987; 88(1):47-52.

Dziembor-Gryszkiewicz E, Fikus M, Kazimierczuk Z, Ostrowski W. Activity of human prostatic acid phosphatase toward purine 5'-phosphonucleosides. Bull Acad Pol Sci Biol. 1978; 26(12):815-21.

Griffiths J C. Prostate-specific acid phosphatase: re-evaluation of radioimmunoassay in diagnosing prostatic disease. Clin Chem. 1980 March; 26(3): 433-6.

Gundlach B R, Reiprich S, Sopper S, Means R E, Dittmer U, Matz-Rensing K, Stahl-Hennig C, Uberla K. Env-independent protection induced by live, attenuated simian immunodeficiency virus vaccines. J Virol. 1998 October; 72(10): 7846-51.

Hakalahti L, Vihko P, Henttu P, Autio-Harmainen H, Soini Y, Vihko R. Evaluation of PAP and PSA gene expression in prostatic hyperplasia and prostatic carcinoma using northern-blot analyses, in situ hybridization and immunohistochemical stainings with monoclonal and bispecific antibodies. Int J Cancer. 1993 Oct. 21; 55(4):590-7.

He J, Landau N R. Use of a novel human immunodeficiency virus type 1 reporter virus expressing human placental alkaline phosphatase to detect an alternative viral receptor. J Virol. 1995 July; 69(7):4587-92.

Kamoshida S, Tsutsumi Y. Extraprostatic localization of prostatic acid phosphatase and prostate-specific antigen: distribution in cloacogenic glandular epithelium and sex-dependent expression in human anal gland. Hum Pathol. 1990 November; 21(11):1108-11.

Kuciel R, Bakalova A, Mazurkiewicz A, Bilska A, Ostrowski W. Is the subunit of prostatic phosphatase active? Reversible denaturation of prostatic acid phosphatase. Biochem Int. 1990 October; 22(2):329-34.

Lee C L, Li S S, Chu T M. Immunologically reactive tryptic fragments of human prostatic acid phosphatase. Biochem J. 1984 Nov. 1; 223(3):871-7.

Luchter-Wasyl E, Ostrowski W. Subunit structure of human prostatic acid phosphatase. Biochim Biophys Acta. 1974 Oct. 9; 365(2):349-59.

Munch J, Standker L, Pöhlmann S, Baribaud F, Papkalla A, Rosorius O, Stauber R, Sass G, Heveker N, Adermann K, Escher S, Kluver E, Doms R W, Forssmann W G, Kirchhoff F. Hemofiltrate C C chemokine 1[9-74] causes effective internalization of CCR5 and is a potent inhibitor of R5-tropic human immunodeficiency virus type 1 strains in primary T cells and macrophages. Antimicrob Agents Chemother. 2002 April; 46(4):982-90.

Nilsson M R. Techniques to study amyloid fibril formation in vitro. Methods 2004, 34, 151-160.

Papkalla A, Munch J, Otto C, Kirchhoff F. Nef enhances human immunodeficiency virus type 1 infectivity and replication independently of viral coreceptor tropism. J Virol. 2002 August; 76(16):8455-9.

Pohlmann S, Krumbiegel M, Kirchhoff F. Coreceptor usage of BOB/GPR15 and Bonzo/STRL33 by primary isolates of human immunodeficiency virus type 1. J Gen Virol. 1999 May; 80 (Pt 5):1241-51.

Risley J M, Van Etten R L. Structures of the carbohydrate moieties of human prostatic acid phosphatase elucidated by H1 nuclear magnetic resonance spectroscopy. Arch Biochem Biophys. 1987 Nov. 1; 258(2):404-12.

Ronnberg L, Vihko P, Sajanti E, Vihko R. Clomiphene citrate administration to normogonadotropic subfertile men: blood hormone changes and activation of acid phosphatase in seminal fluid. Int J Androl. 1981 June; 4(3):372-8.

Schiff D, Chan G, Poznansky M J. Bilirubin toxicity in neural cell lines N115 and NBR10A. Pediatr Res. 1985 September; 19(9):908-11.

Sharief F S, Li S S. Structure of human prostatic acid phosphatase gene. Biochem Biophys Res Commun. 1992 May 15; 184(3):1468-76

Shaw L M, Yang N, Brooks J J, Neat M, Marsh E, Seamonds B. Immunochemical evaluation of the organ specificity of prostatic acid phosphatase. Clin Chem. 1981 September; 27(9):1505-12.

Vihko P, Kontturi M, Korhonen L K. Purification of human prostatic acid phosphatase by affinity chromatography and isoelectric focusing. Part I. Clin Chem. 1978 March; 24(3): 466-70.

Vihko P. Characterization of the principal human prostatic acid phosphatase isoenzyme, purified by affinity chromatography and isoelectric focusing. Part II. Clin Chem. 1978 October; 24(10):1783-87.

Vihko P, Kostama A, Janne O, Sajanti E, Vihko R. Rapid radioimmunoassay for prostate-specific acid phosphatase in human serum. Clin Chem. 1980 October; 26(11): 1544-7.

Vihko P, Lukkarinen O, Kontturi M, Vihko R. Effectiveness of radioimmunoassay of human prostate-specific acid phosphatase in the diagnosis and follow-up of therapy in prostatic carcinoma. Cancer Res. 1981 March; 41(3): 1180-3.

Vihko P, Virkkunen P, Henttu P, Roiko K, Solin T, Huhtala M L. Molecular cloning and sequence analysis of cDNA encoding human prostatic acid phosphatase. FEBS Lett. 1988 Aug. 29; 236(2):275-81.

Vihko P, Kurkela R, Porvari K, Herrala A, Lindfors A, Lindqvist Y, Schneider G. Rat acid phosphatase: overexpression of active, secreted enzyme by recombinant baculovirus-infected insect cells, molecular properties, and crystallization. Proc Natl Acad Sci USA. 1993 Feb. 1; 90(3):799-803.

Waheed A, Van Etten R L. Biosynthesis and processing of lysosomal acid phosphatase in cultured human cells. Arch Biochem Biophys. 1985 Nov. 15; 243(1):274-83.

Wasylewska E, Czubak J, Ostrowski W S. Phosphoprotein phosphatase activity of human prostate acid phosphatase. Acta Biochim Pol. 1983; 30(2):175-84.

Wei X, Decker J M, Liu H, Zhang Z, Arani R B, Kilby J M, Saag M S, Wu X, Shaw G M, Kappes J C. Emergence of resistant human immunodeficiency virus type 1 in patients receiving fusion inhibitor (T-20) monotherapy. Antimicrob Agents Chemother. 2002 June; 46(6):1896-905.

Westermark, P. Aspects on human amyloid forms and their fibril polypeptides. FEBS J. 2005; 272, 5942-5949.

Wojtowicz W M, Farzan M, Joyal J L, Carter K, Babcock G J, Israel D I, Sodroski J, Mirzabekov T. Stimulation of enveloped virus infection by beta-amyloid fibrils. J Biol. Chem. 2002 Sep. 20; 277(38):35019-24.

Yam L T, Janckila A J, Li C Y, Lam W K. Presence of "prostatic" acid phosphatase in human neutrophils. Invest Urol. 1981 July; 19(1):34-8.

The invention claimed is:

1. A method for promoting entry of a retrovirus, a retrovirus particle, a retrovirus vector, or a retrovirus-based vaccine into a cell, comprising providing to the cell:

(i) an isolated peptide having an amino acid sequence of: R1-KEKSRLQGGVLVNEILNHMKRATQIPSYKK-R2 (SEQ ID NO:19);

wherein R1 is H, YGIHKQ (SEQ ID NO:20), GIHKQ (SEQ ID NO:21), IHKQ (SEQ ID NO:22), HKQ, KQ, or Q;

wherein R2 is COOH, LIMY (SEQ ID NO:23), LIM, LI, or L;

wherein the isolated peptide is not the peptide of SEQ ID NO:18; and (ii) a retrovirus, a retrovirus particle, a retrovirus vector, or a retrovirus-based vaccine.

2. The method of claim 1, wherein the retrovirus is an oncovirus.

3. The method of claim 1, wherein the retrovirus is a lentivirus.

4. The method of claim 1, wherein the retrovirus is Human Immunodeficiency Virus (HIV), Simian Immunodeficiency Virus (SIV), Murine Leukemia Virus (MuLV), foamy virus, Hepatitis B Virus (HBV), Hepatitis C Virus (HCV), or Vesicular Stomatitis Virus (VSV).

5. The method of claim 1, wherein the retrovirus is HIV.

6. The method of claim 1, wherein the method promotes entry of a retrovirus.

7. The method of claim 1, wherein the method promotes entry of a retrovirus particle.

8. The method of claim 1, wherein the method promotes entry of a retrovirus vector.

9. The method of claim 1, wherein the method promotes entry of a retrovirus-based vaccine.

10. A method for enhancing delivery of an exogenous gene contained in a retrovirus vector to a cell, comprising providing to the cell:

(i) an isolated peptide having an amino acid sequence of: R1-KEKSRLQGGVLVNEILNHMKRATQIPSYKK-R2 (SEQ ID NO:19);

wherein R1 is H, YGIHKQ (SEQ ID NO:20), GIHKQ (SEQ ID NO:21), IHKQ (SEQ ID NO:22), HKQ, KQ, or Q;

wherein R2 is COOH, LIMY (SEQ ID NO:23), L M, LI, or L;

wherein the isolated peptide is not the peptide of SEQ ID NO:18; and (ii) a retrovirus vector containing an exogenous gene;

wherein the isolated peptide enhances delivery of the exogenous gene compared to delivery of the exogenous gene in the absence of the isolated peptide.

11. The method of claim 10, wherein the retrovirus is an oncovirus.

12. The method of claim 10, wherein the retrovirus is a lentivirus.

13. The method of claim 10, wherein the retrovirus is HIV, SIV, MuLV, foamy virus, HBV, HCV, or VSV.

14. The method of claim 10, wherein the retrovirus is HIV.

15. The method of claim 10, wherein the retrovirus vector is used for gene therapy.

* * * * *

SEQUENCE LISTING

```
<160> NUMBER OF SEQ ID NOS: 23

<210> SEQ ID NO 1
<211> LENGTH: 40
<212> TYPE: PRT
<213> ORGANISM: Artificial Sequence
<220> FEATURE:
<223> OTHER INFORMATION: Synthetic fragment of the PAP protein

<400> SEQUENCE: 1

Tyr Gly Ile His Lys Gln Lys Glu Lys Ser Arg Leu Gln Gly Gly Val
1               5                   10                  15

Leu Val Asn Glu Ile Leu Asn His Met Lys Arg Ala Thr Gln Ile Pro
            20                  25                  30

Ser Tyr Lys Lys Leu Ile Met Tyr
        35                  40

<210> SEQ ID NO 2
<211> LENGTH: 39
<212> TYPE: PRT
<213> ORGANISM: Artificial Sequence
<220> FEATURE:
<223> OTHER INFORMATION: Synthetic fragment of the PAP protein

<400> SEQUENCE: 2

Gly Ile His Lys Gln Lys Glu Lys Ser Arg Leu Gln Gly Gly Val Leu
1               5                   10                  15

Val Asn Glu Ile Leu Asn His Met Lys Arg Ala Thr Gln Ile Pro Ser
            20                  25                  30

Tyr Lys Lys Leu Ile Met Tyr
        35

<210> SEQ ID NO 3
<211> LENGTH: 38
<212> TYPE: PRT
<213> ORGANISM: Artificial Sequence
<220> FEATURE:
<223> OTHER INFORMATION: Synthetic fragment of the PAP protein

<400> SEQUENCE: 3

Ile His Lys Gln Lys Glu Lys Ser Arg Leu Gln Gly Gly Val Leu Val
1               5                   10                  15

Asn Glu Ile Leu Asn His Met Lys Arg Ala Thr Gln Ile Pro Ser Tyr
            20                  25                  30

Lys Lys Leu Ile Met Tyr
        35

<210> SEQ ID NO 4
<211> LENGTH: 37
```

<212> TYPE: PRT
<213> ORGANISM: Artificial Sequence
<220> FEATURE:
<223> OTHER INFORMATION: Synthetic fragment of the PAP protein

<400> SEQUENCE: 4

His Lys Gln Lys Glu Lys Ser Arg Leu Gln Gly Gly Val Leu Val Asn
1               5                   10                  15

Glu Ile Leu Asn His Met Lys Arg Ala Thr Gln Ile Pro Ser Tyr Lys
            20                  25                  30

Lys Leu Ile Met Tyr
        35

<210> SEQ ID NO 5
<211> LENGTH: 36
<212> TYPE: PRT
<213> ORGANISM: Artificial Sequence
<220> FEATURE:
<223> OTHER INFORMATION: Synthetic fragment of the PAP protein

<400> SEQUENCE: 5

Lys Gln Lys Glu Lys Ser Arg Leu Gln Gly Gly Val Leu Val Asn Glu
1               5                   10                  15

Ile Leu Asn His Met Lys Arg Ala Thr Gln Ile Pro Ser Tyr Lys Lys
            20                  25                  30

Leu Ile Met Tyr
        35

<210> SEQ ID NO 6
<211> LENGTH: 35
<212> TYPE: PRT
<213> ORGANISM: Artificial Sequence
<220> FEATURE:
<223> OTHER INFORMATION: Synthetic fragment of the PAP protein

<400> SEQUENCE: 6

Gln Lys Glu Lys Ser Arg Leu Gln Gly Gly Val Leu Val Asn Glu Ile
1               5                   10                  15

Leu Asn His Met Lys Arg Ala Thr Gln Ile Pro Ser Tyr Lys Lys Leu
            20                  25                  30

Ile Met Tyr
        35

<210> SEQ ID NO 7
<211> LENGTH: 34
<212> TYPE: PRT
<213> ORGANISM: Artificial Sequence
<220> FEATURE:
<223> OTHER INFORMATION: Synthetic fragment of the PAP protein

<400> SEQUENCE: 7

Lys Glu Lys Ser Arg Leu Gln Gly Gly Val Leu Val Asn Glu Ile Leu
1               5                   10                  15

Asn His Met Lys Arg Ala Thr Gln Ile Pro Ser Tyr Lys Lys Leu Ile
            20                  25                  30

Met Tyr

<210> SEQ ID NO 8
<211> LENGTH: 38
<212> TYPE: PRT
<213> ORGANISM: Artificial Sequence
<220> FEATURE:
<223> OTHER INFORMATION: Synthetic fragment of the PAP protein -continued

```
<400> SEQUENCE: 8

Gly Ile His Lys Gln Lys Glu Lys Ser Arg Leu Gln Gly Gly Val Leu
1               5                   10                  15

Val Asn Glu Ile Leu Asn His Met Lys Arg Ala Thr Gln Ile Pro Ser
            20                  25                  30

Tyr Lys Lys Leu Ile Met
        35

<210> SEQ ID NO 9
<211> LENGTH: 37
<212> TYPE: PRT
<213> ORGANISM: Artificial Sequence
<220> FEATURE:
<223> OTHER INFORMATION: Synthetic fragment of the PAP protein

<400> SEQUENCE: 9

Gly Ile His Lys Gln Lys Glu Lys Ser Arg Leu Gln Gly Gly Val Leu
1               5                   10                  15

Val Asn Glu Ile Leu Asn His Met Lys Arg Ala Thr Gln Ile Pro Ser
            20                  25                  30

Tyr Lys Lys Leu Ile
        35

<210> SEQ ID NO 10
<211> LENGTH: 36
<212> TYPE: PRT
<213> ORGANISM: Artificial Sequence
<220> FEATURE:
<223> OTHER INFORMATION: Synthetic fragment of the PAP protein

<400> SEQUENCE: 10

Gly Ile His Lys Gln Lys Glu Lys Ser Arg Leu Gln Gly Gly Val Leu
1               5                   10                  15

Val Asn Glu Ile Leu Asn His Met Lys Arg Ala Thr Gln Ile Pro Ser
            20                  25                  30

Tyr Lys Lys Leu
        35

<210> SEQ ID NO 11
<211> LENGTH: 35
<212> TYPE: PRT
<213> ORGANISM: Artificial Sequence
<220> FEATURE:
<223> OTHER INFORMATION: Synthetic fragment of the PAP protein

<400> SEQUENCE: 11

Gly Ile His Lys Gln Lys Glu Lys Ser Arg Leu Gln Gly Gly Val Leu
1               5                   10                  15

Val Asn Glu Ile Leu Asn His Met Lys Arg Ala Thr Gln Ile Pro Ser
            20                  25                  30

Tyr Lys Lys
        35

<210> SEQ ID NO 12
<211> LENGTH: 36
<212> TYPE: PRT
<213> ORGANISM: Artificial Sequence
<220> FEATURE:
<223> OTHER INFORMATION: Synthetic fragment of the PAP protein

<400> SEQUENCE: 12

Tyr Gly Ile His Lys Gln Lys Glu Lys Ser Arg Leu Gln Gly Gly Val
1               5                   10                  15
```

```
Leu Val Asn Glu Ile Leu Asn His Met Lys Arg Ala Thr Gln Ile Pro
            20                  25                  30

Ser Tyr Lys Lys
        35

<210> SEQ ID NO 13
<211> LENGTH: 19
<212> TYPE: PRT
<213> ORGANISM: Artificial Sequence
<220> FEATURE:
<223> OTHER INFORMATION: Synthetic fragment of the PAP protein

<400> SEQUENCE: 13

Gly Ile His Lys Gln Lys Glu Lys Ser Arg Leu Gln Gly Gly Val Leu
1               5                   10                  15

Val Asn Glu

<210> SEQ ID NO 14
<211> LENGTH: 16
<212> TYPE: PRT
<213> ORGANISM: Artificial Sequence
<220> FEATURE:
<223> OTHER INFORMATION: Synthetic fragment of the PAP protein

<400> SEQUENCE: 14

Ile Leu Asn His Met Lys Arg Ala Thr Gln Ile Pro Ser Tyr Lys Lys
1               5                   10                  15

<210> SEQ ID NO 15
<211> LENGTH: 28
<212> TYPE: PRT
<213> ORGANISM: Artificial Sequence
<220> FEATURE:
<223> OTHER INFORMATION: Synthetic control protein
<220> FEATURE:
<221> NAME/KEY: MOD_RES
<222> LOCATION: (1)..(1)
<223> OTHER INFORMATION: ACETYLATION

<400> SEQUENCE: 15

Ser Asp Ala Ala Val Asp Thr Ser Ser Glu Ile Thr Thr Lys Asp Leu
1               5                   10                  15

Lys Glu Lys Lys Glu Val Val Glu Glu Ala Glu Asn
            20                  25

<210> SEQ ID NO 16
<211> LENGTH: 41
<212> TYPE: PRT
<213> ORGANISM: Artificial Sequence
<220> FEATURE:
<223> OTHER INFORMATION: Synthetic control protein
<220> FEATURE:
<221> NAME/KEY: MOD_RES
<222> LOCATION: (41)..(41)
<223> OTHER INFORMATION: AMIDATION

<400> SEQUENCE: 16

Ser Glu Glu Pro Pro Ile Ser Leu Asp Leu Thr Phe His Leu Leu Arg
1               5                   10                  15

Glu Val Leu Glu Met Ala Arg Ala Glu Gln Leu Ala Gln Gln Ala His
            20                  25                  30

Ser Asn Arg Lys Leu Met Glu Ile Ile
        35                  40

<210> SEQ ID NO 17
```

```
<211> LENGTH: 31
<212> TYPE: PRT
<213> ORGANISM: Artificial Sequence
<220> FEATURE:
<223> OTHER INFORMATION: Synthetic control protein
<220> FEATURE:
<221> NAME/KEY: MOD_RES
<222> LOCATION: (31)..(31)
<223> OTHER INFORMATION: AMIDATION

<400> SEQUENCE: 17

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 18
<211> LENGTH: 18
<212> TYPE: PRT
<213> ORGANISM: Artificial Sequence
<220> FEATURE:
<223> OTHER INFORMATION: Synthetic fragment of the PAP protein

<400> SEQUENCE: 18

Gly Gly Val Leu Val Asn Glu Ile Leu Asn His Met Lys Arg Ala Thr
1               5                   10                  15

Gln Ile

<210> SEQ ID NO 19
<211> LENGTH: 30
<212> TYPE: PRT
<213> ORGANISM: Artificial Sequence
<220> FEATURE:
<223> OTHER INFORMATION: Synthetic fragment of the PAP protein

<400> SEQUENCE: 19

Lys Glu Lys Ser Arg Leu Gln Gly Gly Val Leu Val Asn Glu Ile Leu
1               5                   10                  15

Asn His Met Lys Arg Ala Thr Gln Ile Pro Ser Tyr Lys Lys
            20                  25                  30

<210> SEQ ID NO 20
<211> LENGTH: 6
<212> TYPE: PRT
<213> ORGANISM: Artificial Sequence
<220> FEATURE:
<223> OTHER INFORMATION: Synthetic fragment of the PAP protein

<400> SEQUENCE: 20

Tyr Gly Ile His Lys Gln
1               5

<210> SEQ ID NO 21
<211> LENGTH: 5
<212> TYPE: PRT
<213> ORGANISM: Artificial Sequence
<220> FEATURE:
<223> OTHER INFORMATION: Synthetic fragment of the PAP protein

<400> SEQUENCE: 21

Gly Ile His Lys Gln
1               5

<210> SEQ ID NO 22
<211> LENGTH: 4
<212> TYPE: PRT
<213> ORGANISM: Artificial Sequence
```

-continued

<220> FEATURE:
<223> OTHER INFORMATION: Description of Artificial Sequence: fragment of the PAP protein

<400> SEQUENCE: 22

Ile His Lys Gln
1

<210> SEQ ID NO 23
<211> LENGTH: 4
<212> TYPE: PRT
<213> ORGANISM: Artificial Sequence
<220> FEATURE:
<223> OTHER INFORMATION: Synthetic fragment of the PAP protein

<400> SEQUENCE: 23

Leu Ile Met Tyr
1